US009937363B2

(12) United States Patent
Takizawa et al.

(10) Patent No.: US 9,937,363 B2

(45) Date of Patent: Apr. 10, 2018

(54) PARTICLE BEAM IRRADIATION SYSTEM

(71) Applicant: Hitachi, Ltd., Tokyo (JP)

(72) Inventors: Kenichi Takizawa, Tokyo (JP); Hidehito Asano, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/154,090

(22) Filed: May 13, 2016

(65) Prior Publication Data

US 2016/0332002 A1 Nov. 17, 2016

(30) Foreign Application Priority Data

May 14, 2015 (JP) ................................ 2015-098743

(51) Int. Cl.

*A61N 5/00* (2006.01)
*A61N 5/10* (2006.01)
*H05H 9/00* (2006.01)
*H05H 13/04* (2006.01)
*H05H 7/00* (2006.01)

(52) U.S. Cl.

CPC ........... *A61N 5/1081* (2013.01); *A61N 5/103* (2013.01); *A61N 5/1049* (2013.01); *H05H 9/00* (2013.01); *H05H 13/04* (2013.01); *A61N 5/1043* (2013.01); *A61N 5/1069* (2013.01); *A61N 2005/1087* (2013.01); *H05H 2007/002* (2013.01); *H05H 2277/11* (2013.01)

(58) Field of Classification Search

CPC .... A61N 5/1081; A61N 5/103; A61N 5/1049; H05H 9/00; H05H 13/04; H05H 2007/002; H05H 2277/11

USPC .... 250/396 R, 397, 398, 492.1, 492.2, 492.3

See application file for complete search history.

(56) References Cited

U.S. PATENT DOCUMENTS 4,969,170 A * 11/1990 Kikuchi .................. A61N 5/10 378/114
5,039,867 A 8/1991 Nishihara et al.
2006/0027766 A1 2/2006 Matsuda et al.
2006/0163495 A1 7/2006 Hiramoto et al.

FOREIGN PATENT DOCUMENTS

JP 01-209077 A 8/1989
JP 08-257023 A 10/1996
JP 09-140700 A 6/1997
JP 2004-358237 A 12/2004
JP 2006-239403 A 9/2006
JP 2011-092444 A 5/2011

* cited by examiner

*Primary Examiner* — Nicole Ippolito
*Assistant Examiner* — Hanway Chang
(74) *Attorney, Agent, or Firm* — Mattingly & Malur, PC

(57) ABSTRACT

An irradiation apparatus attached to a rotary gantry includes a middle housing unit and a lower housing unit. Touch sensor apparatuses are attached to a middle housing unit, and touch sensor apparatuses are attached to a lower housing unit. The touch sensor apparatus includes a cover, a pair of cover support apparatuses for attaching the cover to a support member of the middle housing unit, and a sensor unit attached to each cover support apparatus. When the cover comes into contact with a bed and moves toward the support member during rotation of the irradiation apparatus, a link such as a cover support apparatus activates the sensor unit, and a contact signal is output. The touch sensor apparatuses also function in the same manner.

17 Claims, 13 Drawing Sheets

NOZZLE CONTROL APPARATUS
SCAN CONTROL APPARATUS
BED CONTROL APPARATUS
GANTRY CONTROL APPARATUS
TREATMENT PLAN APPARATUS
DATABASE
MEMORY
CPU
CENTRAL CONTROL APPARATUS
ACCELERATION DEVICE AND TRANSPORT SYSTEM CONTROL APPARATUS
94A, 94B 39
50
47
49
51
33A
52
48
102
29
43
III
40
45
31A
34
41
42
42
46
21
28
27
28A
44
31B
28
30
127
16
33B 1A
2A
119
120A
120B
118
124
125
126
121
122
123
18
15
16
17
19
19
127
22
28A
20
25
26
21
23
24
27
34
35
36
37
38
39
76
102
94A, 94B
83
NOZZLE CONTROL APPARATUS
SCAN CONTROL APPARATUS
114
BED CONTROL APPARATUS
115
GANTRY CONTROL APPARATUS
113
ACCELERATION DEVICE AND TRANSPORT SYSTEM CONTROL APPARATUS
112
CPU
110
MEMORY
111
CENTRAL CONTROL APPARATUS
109
DATABASE
116
TREATMENT PLAN APPARATUS
117
108

PARTICLE BEAM IRRADIATION SYSTEM

CLAIM OF PRIORITY

The present application claims priority from Japanese Patent application serial no. 2015-098743, filed on May 14, 2015, the content of which is hereby incorporated by reference into this application.

BACKGROUND OF THE INVENTION

1. Field of the Invention

The present invention relates to a particle beam irradiation system, and more particularly, to a particle beam irradiation system preferably applied to cancer treatment.

2. Description of the Related Art

When particle beam irradiation system are roughly classified, a particle beam irradiation system having a synchrotron as an accelerator (for example, see Japanese Patent Laid-Open No. 2004-358237), and a particle beam irradiation system having a cyclotron as an accelerator (for example, see Japanese Patent Laid-Open No. 2011-92444) are known as the particle beam irradiation system.

The particle beam irradiation system having the synchrotron includes an ion source, a linear accelerator, a synchrotron, a high energy beam transport system (hereinafter referred to as HEBT system), a gantry beam transport system (hereinafter referred to as GABT system), a rotary gantry, and an irradiation apparatus. A proton ion beam (or carbon ion beam) passing through a linear accelerator and being accelerated by a synchrotron to a preselected energy is emitted to an HEBT system, and passes through a GABT system, and the proton ion beam (or carbon ion beam) reaches an irradiation apparatus attached to a rotary gantry. A proton ion beam (hereinafter referred to as ion beam) is irradiated from the irradiation apparatus to an affected area of a cancer of a patient who lies on a treatment bed.

A particle beam irradiation system having a cyclotron includes an ion source, a cyclotron, an HEBT system, a GABT system, a rotary gantry, and an irradiation apparatus. The HEBT system, the GABT system, the rotary gantry, and the irradiation apparatus in the particle beam irradiation system having the cyclotron are substantially the same as the structures thereof in the particle beam irradiation system having the synchrotron. An ion beam accelerated and emitted from the cyclotron passes through the HEBT system and GABT system, and is irradiated from the irradiation apparatus to the affected area.

By the way, as illustrated in FIG. 1 of Japanese Patent Laid-Open No. H8-257023, the X ray CT apparatus has a bed and a gantry having an opening portion formed in a horizontal direction. An X ray tube generating an X ray is provided in a gantry so as to rotate around the opening portion formed in the gantry. The bed includes a bed base and a top board provided above the bed base and moving in a horizontal direction toward the opening portion. While a subject is lying on the top board, the top board as well as the subject are inserted into the opening portion, and an X ray discharged from the X ray tube is irradiated to the subject while rotating the X ray tube around the opening portion. Japanese Patent Laid-Open No. H9-140700 also describes a similar X ray CT apparatus.

These X ray CT apparatuses described in these publications are each provided with a touch sensor provided on a side surface of the gantry at the bed side and near the opening portion. When, in particular, the gantry is inclined, this touch sensor detects a contact with the touch sensor by the top board moving in the horizontal direction or the subject lying on the top board. When the touch sensor detects this contact, the movement of the top board is stopped.

Further, the particle beam irradiation system needs to fix the position of the affected area of the patient on the bed with respect to the irradiation apparatus, before the ion beam emitted by the accelerator is irradiated from the irradiation apparatus onto the affected area of the patient lying on the bed. An example of a method for fixing the position of the affected area with respect to the irradiation apparatus is described in Japanese Patent Laid-Open No. H1-209077. In the position determination of the position of the affected area in Japanese Patent Laid-Open No. H1-209077, the amount of movement of the bed for the determination of the position of the affected area is calculated by using reference image information generated on the basis of tomographic image information obtained in advance with an X ray CT apparatus before the determination of the position of the affected area and each piece of current X ray image information in two directions perpendicular to each other which are generated on the basis of X ray detection signals from an X ray detection apparatus located below the bed so as to face the X ray source provided in the irradiation apparatus while the bed on which the patient is lying is moved so that the affected area of the patient faces the irradiation apparatus before the ion beam is irradiated. The position of the affected area with respect to the irradiation apparatus is determined by manually moving the bed on the basis of the amount of movement of the bed that has been calculated. Japanese Patent Laid-Open No. H1-209077 indicates that the bed is automatically moved on the basis of the amount of movement of the bed thus calculated. It should be noted that Japanese Patent Laid-Open No. 2006-239403 also indicates that the amount of movement of the bed the rotation angle of the bed are calculated, and the bed control apparatus automatically determines the position of the affected area with respect to the irradiation apparatus on the basis of the amount of movement and the rotation angle thus calculated.

SUMMARY OF THE INVENTION

In the particle beam irradiation system, the center axis of the irradiation apparatus is required to be set in the irradiation direction of the ion beam to the affected area of the patient that is planned in a treatment plan by rotating the rotary gantry before the ion beam from the irradiation apparatus is irradiated to the affected area of the patient lying on the bad. In a case where the position of the affected area is determined by manually moving the bed, an engineer who enters into the treatment chamber of the rotary gantry monitors the movement of the bed, and the engineer checks an interference between the irradiation apparatus rotated by the rotary gantry and the bed and the like.

In order to determine the position of the affected area, a method of automatically moving the bed by control is studied as described above. In the automatic control of the movement of the bed, in case an abnormality occurs in the automatic control, and the bed is located outside of the track of the tip of the rotating irradiation apparatus, the rotating irradiation apparatus may come into contact with the bed (or the patient). A method is studied to install a monitor camera in the treatment chamber formed in the rotary gantry in which the irradiation apparatus is disposed and monitor the movement of the automatically moved bed and whether the bed has reached a predetermined position to alleviate a contact between the irradiation apparatus and the bed (or the patient) as described above. However, with only the monitoring with the monitor camera, it may be impossible to prevent the contact thereof in advance.

Therefore, it is preferable to achieve a particle beam irradiation system capable of avoiding such contact even in a case where the movement of the bed is automatically controlled.

It is an object of the present invention to provide a particle beam irradiation system capable of avoiding a possibility of contact between an irradiation apparatus and a bed.

A feature of the present invention in order to achieve the above object is to provide a particle beam irradiation system including: an accelerator accelerating an ion beam; and an irradiation apparatus guiding the ion beam emitted from the accelerator, wherein the irradiation apparatus includes a touch sensor apparatus detecting a force applied from a direction crossing a center axis of the irradiation apparatus.

When a bed on which a patient is lying comes into contact with a touch sensor apparatus of an irradiation apparatus, this touch sensor apparatus can detect the contact, and can stop the movement of the bed. Therefore, a damage in at least one of the irradiation apparatus and the bed can be avoided.

According to the present invention, in a particle beam treatment system, a damage in at least one of the irradiation apparatus and the bed can be avoided.

DESCRIPTION OF THE PREFERRED EMBODIMENTS

Figure 1:
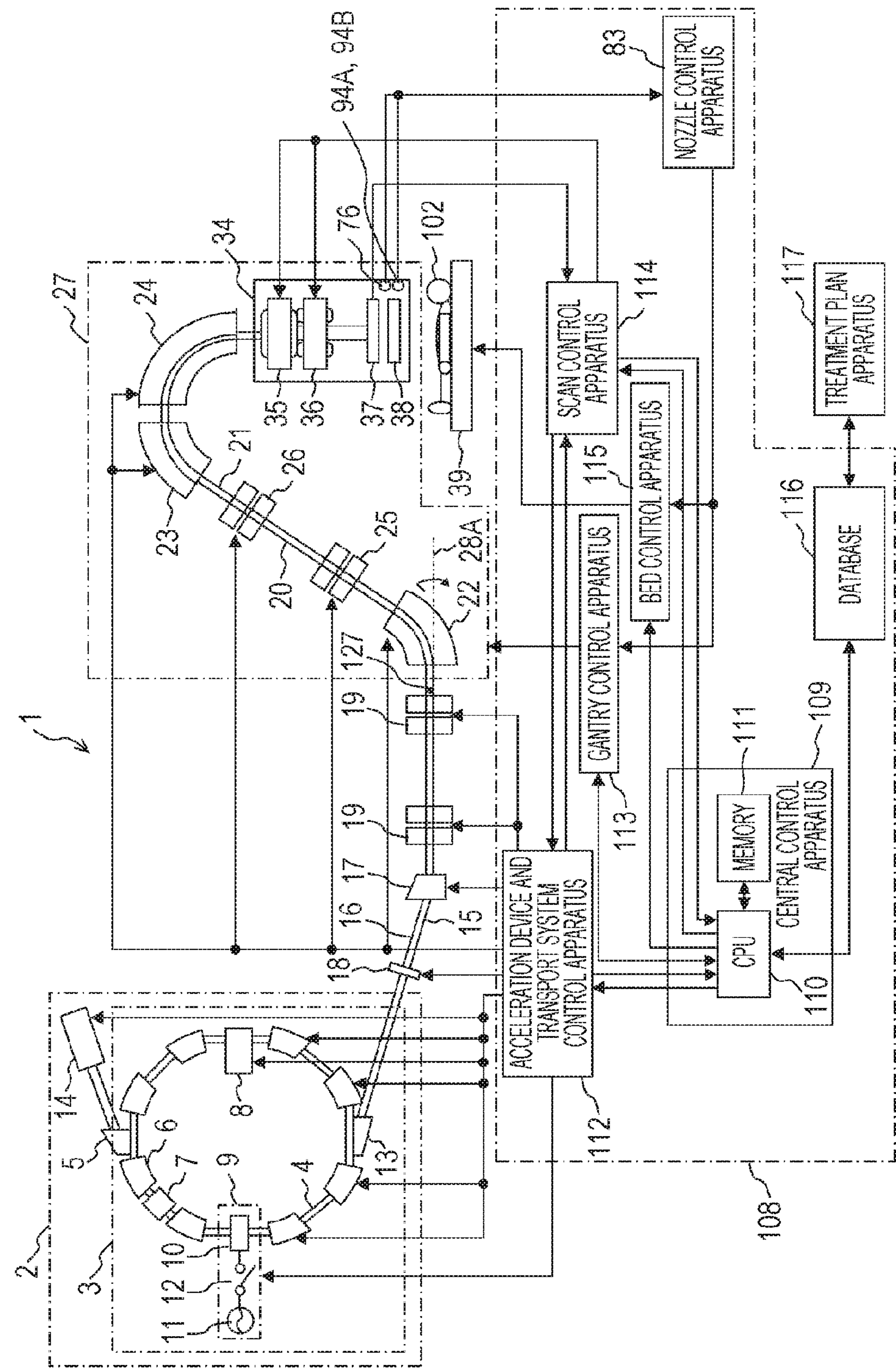
FIG. 1 is a configuration diagram illustrating a particle beam irradiation system according to a first embodiment which is a preferred embodiment of the present invention.

Each embodiment of the present invention will be hereinafter explained.

First Embodiment

A particle beam irradiation system according to the first embodiment which is a preferred embodiment of the present invention will be hereinafter explained with reference to FIG. 1 to FIG. 3.

The particle beam irradiation system 1 according to the present embodiment is provided in a building (not shown) and is installed on a floor surface of a building. As illustrated in FIG. 1, this particle beam irradiation system 1 includes an ion beam generation apparatus 2, a high energy beam transport system (HEBT system) 15, a gantry beam transport system (GABT system) 20, a rotary gantry 27, an irradiation apparatus 34, and a control system 108. In the particle beam irradiation system 1, a proton ion beam is used as an ion beam irradiated to an affected area (beam irradiation target) of a cancer. A carbon ion beam may be used instead of the proton ion beam.

The ion beam generation apparatus 2 includes an ion source (not shown) and a linear accelerator 14 and a synchrotron accelerator 3 which are preceding stage accelerators. The synchrotron accelerator 3 includes an circular beam duct 4 constituting a circular orbit of an ion beam, an injector 5, a radiofrequency acceleration cavity (radiofrequency acceleration apparatus) 8 for applying a radiofrequency voltage to the ion beam, multiple polarization electromagnets 6, multiple quadrupole electromagnets 7, a radiofrequency application apparatus 9 for extraction, and a septum electromagnet 13 for extraction. The injector 5 connected with the beam duct 4 is connected to the linear accelerator 14 by the vacuum duct. The ion source is also connected to the linear accelerator 14. The radiofrequency application apparatus 9 includes an extraction radiofrequency electrode 10, a radiofrequency power supply 11, and an open/close switch 12. The extraction radiofrequency electrode 10 is installed in the beam duct 4 and is connected to the radiofrequency power supply 11 through the open/close switch 12. Each of the polarization electromagnets 6, each of the quadrupole electromagnets 7, the radiofrequency acceleration cavity 8, and the septum electromagnet 13 are disposed along the beam duct 4 as illustrated in FIG. 1.

The HEBT system (first beam transport system) 15 includes a beam path (beam duct) 16 connected to the septum electromagnet 13 of the synchrotron accelerator 3. Multiple quadrupole electromagnets 18, polarization electromagnets 17, and multiple quadrupole electromagnets 19 are disposed in an order from the synchrotron accelerator 3 toward the irradiation apparatus 34 along this beam path 16.

The GABT system (second beam transport system) 20 includes a beam path (beam duct) 21. A polarization electromagnet 22, a quadrupole electromagnets 25, 26, and polarization electromagnets 23 and 24 are arranged from the synchrotron accelerator 3 toward the irradiation apparatus 34 along this beam path 21. Each electromagnet and the beam path 21 of the GABT system 20 are attached to the rotary gantry 27. The beam path 21 is connected to the beam path 16 at a scramble part 127 between the HEBT system 15 and the GABT system 20. The beam path 21 is rotated by the rotary gantry 27, and the beam path 21 is therefore not directly connected to the beam path 16.

The irradiation apparatus 34 includes two scan electromagnets (ion beam scan apparatus) 35 and 36, a beam position monitor 37, and a dose monitor 38. The irradiation apparatus 34 is attached to the rotary gantry 27, and is disposed downstream of the polarization electromagnet 24. The scan electromagnets 35 and 36, the beam position monitor 37, and the dose monitor 38 are arranged in this order along a center axis 107 (see FIG. 4) of the irradiation apparatus 34 toward the ion beam outlet of the irradiation apparatus 34 from the polarization electromagnet 24 in the irradiation apparatus 34. The scan electromagnet 35 bends the ion beam in a plane perpendicular to the center axis 107 of the irradiation apparatus 34, and scans it in an X direction, and the scan electromagnet 36 bends the ion beam in the plane and scans it in a Y direction perpendicular to the X direction. A treatment bed 39 on which a patient 102 lies is disposed so as to be opposite to the tip of the irradiation apparatus 34.

The control system 108 includes a nozzle control apparatus 83, a central control apparatus 109, an acceleration device, and a transport system control apparatus 112, a gantry control apparatus 113, a scan control apparatus 114, a bed control apparatus 115, and a database 116 (see FIG. 1). The central control apparatus 109 includes a central processing unit (CPU) 110 and a memory 111 connected to the CPU 110. The CPU 110 is connected to an acceleration device, and a transport system control apparatus 112, a scan control apparatus 114, a gantry control apparatus 113, and a bed control apparatus 115. The database 116 is connected to the CPU 110. The particle beam irradiation system 1 has a treatment plan apparatus 117, and the treatment plan apparatus 117 is connected to the database 116. The nozzle control apparatus 83 is connected to the gantry control apparatus 113 and the bed control apparatus 115. Further, the nozzle control apparatus 83 is connected to a sensor unit 76 and touch sensors 94A and 94B, explained later, provided in the irradiation apparatus 34.

The rotary gantry 27 will be explained with reference to FIG. 2 and FIG. 3. The rotary gantry 27 includes a cylindrical rotary body 27 having a front ring 29 and a rear ring 30 in a ring shape. The front ring 29 is supported by a support apparatus 31A installed on a floor surface 46 of a building. The rear ring 30 is supported by a support apparatus 31B installed on the floor surface 46. The support apparatus 31A includes a pair of roll support members 32 and multiple support rollers 33A. Multiple support rollers 33A are rotatably attached to the roll support members 32. The front ring 29 is supported by these support rollers 33A. Like the support apparatus 31A, the support apparatus 31B includes a pair of roll support members 32 (not shown) and multiple support rollers 33B. Multiple support rollers 33B are rotatably attached to the roll support members 32. The rear ring 30 is supported by these support rollers 33B. A rotary apparatus (for example, a motor) 44 rotating the rotary gantry 27 is coupled with a rotary shaft of one of the multiple support rollers 33B supporting the rear ring 30. An angle detection device 45 measuring the rotation angle of the rotary gantry 27 is coupled with a rotary shaft of one of the multiple support rollers 33A supporting the front ring 29.

A treatment chamber 40 supported by multiple support members 42 attached to the inner surface of the rotary body 27 is provided in the rotary body 27. A side of the treatment chamber 40 at the front ring 29 is open. A side of the treatment chamber 40 at the rear ring 30 is closed by a separation wall 41. The irradiation apparatus 34 is attached to the rotary body 27, and extends to the center of the rotary body 27, and the irradiation apparatus 34 reaches the treatment cage 43 in the treatment chamber 40. As illustrated in FIG. 2, the beam path 21 of the GABT system 20 connected to the irradiation apparatus 34 extends toward a side at the rear ring 30, and is connected to the beam path 16 of the HEBT system 15 at the scramble part 127 located outside of the rotary gantry 27. It should be noted that the center line 28A (see FIG. 1 and FIG. 2) of the rotary gantry 27 is a rotary center of the rotary gantry 27, and at the scramble part 127, the center line 28A (see FIG. 1 and FIG. 2) passes the center at the entrance of the beam path 21.

Figure 2:
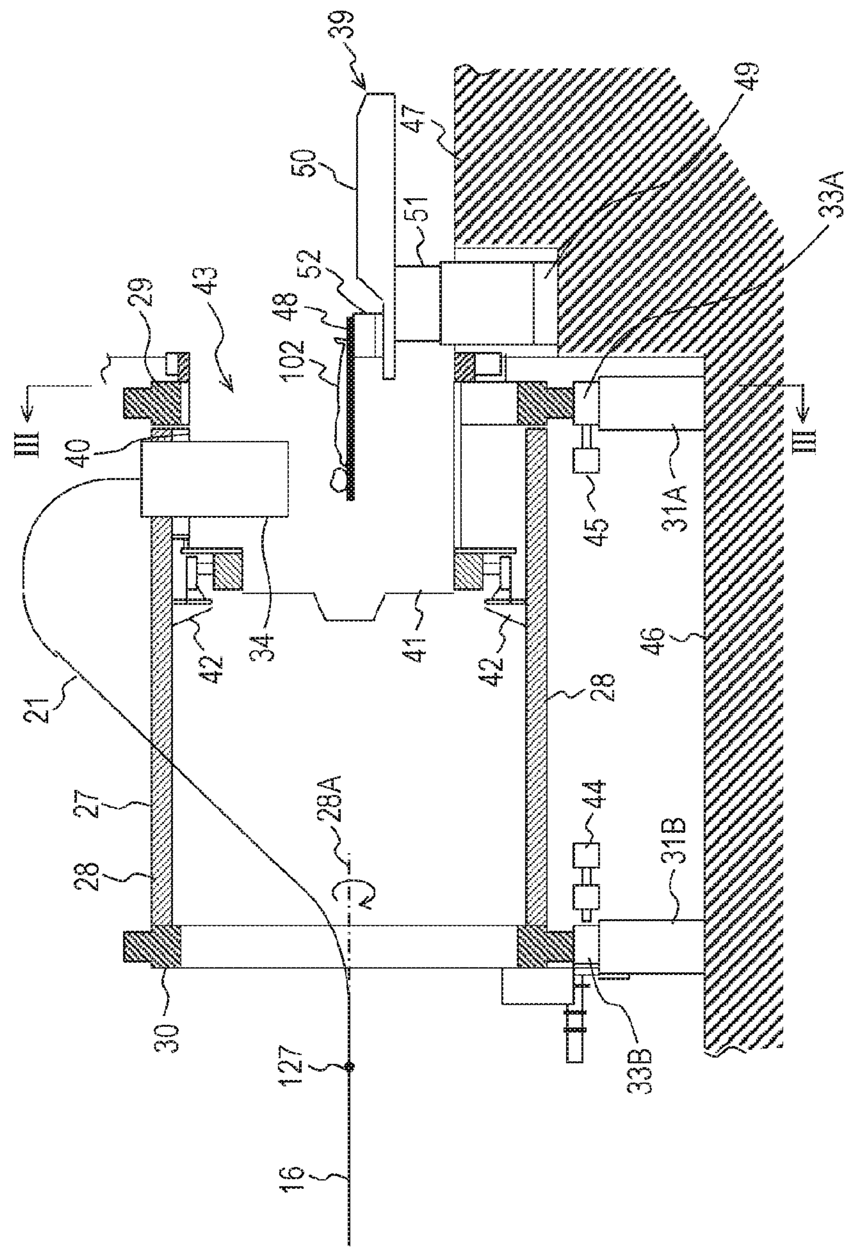
FIG. 2 is an enlarged longitudinal sectional view illustrating a rotary gantry as illustrated in FIG. 1.

As illustrated in FIG. 2, the treatment bed 39 includes a bed 48, an X direction drive mechanism 49, a Y direction drive mechanism 50, an upper and lower direction drive mechanism 51, and a rotary drive mechanism 52. These drive mechanisms are arranged outside of the rotary body 27. The upper and lower direction drive mechanism 51 is disposed on the X direction drive mechanism 49, the Y direction drive mechanism 50 is disposed on the upper and lower direction drive mechanism 51, and the rotary drive mechanism 52 is disposed on the Y direction drive mechanism 50. The bed 48 is disposed on the rotary drive mechanism 52, and is supported by each drive mechanism.

The configuration of the irradiation apparatus 34 will be hereinafter explained in details with reference to FIG. 4 to FIG. 12. The irradiation apparatus 34 includes not only the scan electromagnets 35 and 36, the beam position monitor 37 and the dose monitor 38 explained above, but also an upper housing unit 53A, a middle housing unit 53B, and a lower housing unit 53C, which are housings, and touch sensor apparatuses 61A, 61B, 61C, and 61D. The upper housing unit 53A, the middle housing unit 53B, and the lower housing unit 53C are disposed in this order from the polarization electromagnet 24 located at the most downstream position in the GABT system 20 toward the tip of the irradiation apparatus 34.

The middle housing unit 53B includes a rectangular upper flange 58, a rectangular lower flange 59, and four support pillar members 56. One end portion of each of the four support pillar members 56 is attached to the upper flange 58, and the lower end portion of each of these support pillar members 56 is attached to the lower flange 59. A pair of support members 60A facing each other are disposed in parallel with a gap from each other between the pair of support pillar members 56, and are attached to the upper flange 58 and the lower flange 59. A pair of support members 60B facing each other are disposed in parallel with a gap from each other between the other pair of the support pillar members 56, and are attached to the upper flange 58 and the lower flange 59. The scan electromagnet 36 is disposed between the four support pillar members 56, and is attached to the pair of support members 60A with multiple support members 129, and further, the scan electromagnet 36 is to the pair of support members 60B with multiple support members 130.

The upper housing unit 53A includes a rectangular flange 55, and the scan electromagnet 35 is attached to the flange 55 with multiple support members 128. The flange 55 is disposed on the upper flange 58, and is detachably attached to the upper flange 58. A cover 54 is detachably attached to the flange 55. The cover 54 has four side walls connected to each other so as to enclose the scan electromagnet 35, and is configured to cover the scan electromagnet 35 in a direction of the center axis 107 of the irradiation apparatus 34. It should be noted that a side of the cover 54 at the scan electromagnet 36 is open.

The lower housing unit 53C includes a rectangular upper flange 62, a rectangular lower flange 63, a pair of support members 64A, a pair of support members 64B, and a collimator accommodation unit 65. The pair of support members 64A are disposed in parallel with a gap from each other, and both end portions of these support members 64A are attached to the upper flange 62 and the lower flange 63. The pair of support members 64B are disposed in parallel with a gap from each other, and both end portions of these support members 64A are attached to the upper flange 62 and the lower flange 63. The beam position monitor 37 and the dose monitor 38 are attached to and held by the pair of support members 64A and support members 64B. The collimator accommodation unit 65 is attached to the lower flange 63. The upper flange 62 is in contact with the lower surface of the lower flange 59, and is detachably attached to the lower flange 59.

In the lower housing unit 53C, a cover 104A forming a side wall of the irradiation apparatus 34 is disposed at the side of the separation wall 41 of the irradiation apparatus 34 (see FIG. 5 and FIG. 6), and this cover 104A is fixed to the upper flange 62 and the lower flange 63. Further, in the lower housing unit 53C, a cover 104B forming another side wall of the irradiation apparatus 34 is disposed at the side opposite to the separation wall 41 of the irradiation apparatus 34 (see FIG. 3, FIG. 5 and FIG. 6), and this cover 104B is also fixed to the upper flange 62 and the lower flange 63. In an area where the lower housing unit 53C exists, the covers 104A and 104B form a pair of opposing side walls of the irradiation apparatus 34.

In the middle housing unit 53B, a cover 105A forming a side wall of the irradiation apparatus 34 is disposed at the side of the separation wall 41 of the irradiation apparatus 34 (see FIG. 6), and this cover 105A is fixed to the upper flange 58 and the lower flange 59. Further, in the middle housing unit 53B, a cover 105B forming another side wall of the irradiation apparatus 34 is disposed at the side opposite to the separation wall 41 of the irradiation apparatus 34 (see FIG. 3 and FIG. 6), and this cover 105B is also fixed to the upper flange 62 and the lower flange 63. In an area where the middle housing unit 53B exists, the covers 105A and 105B form a pair of opposing side walls of the irradiation apparatus 34.

Figure 4:
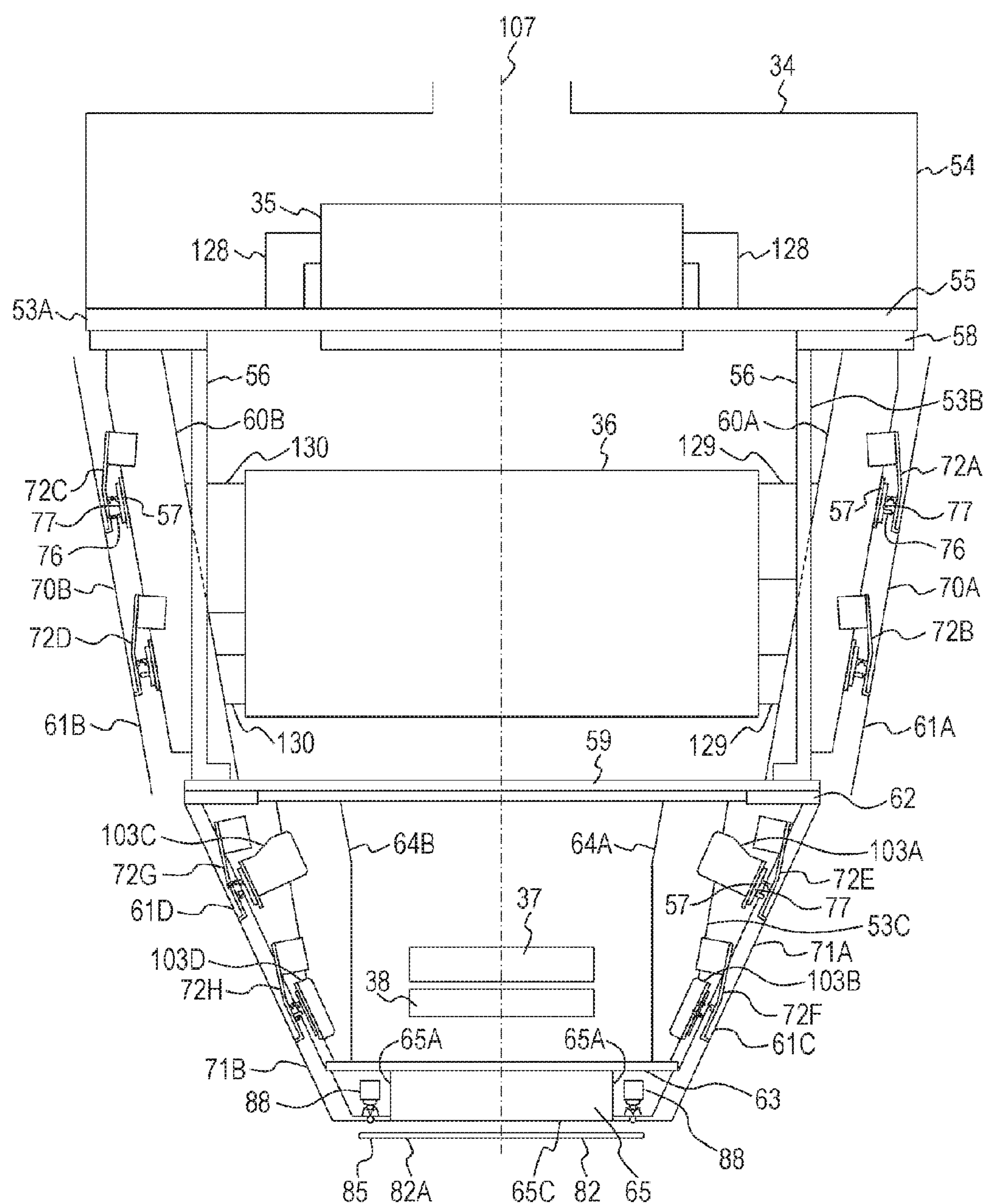
FIG. 4 is a detailed configuration diagram illustrating an irradiation apparatus as illustrated in FIG. 1.
Figure 5:
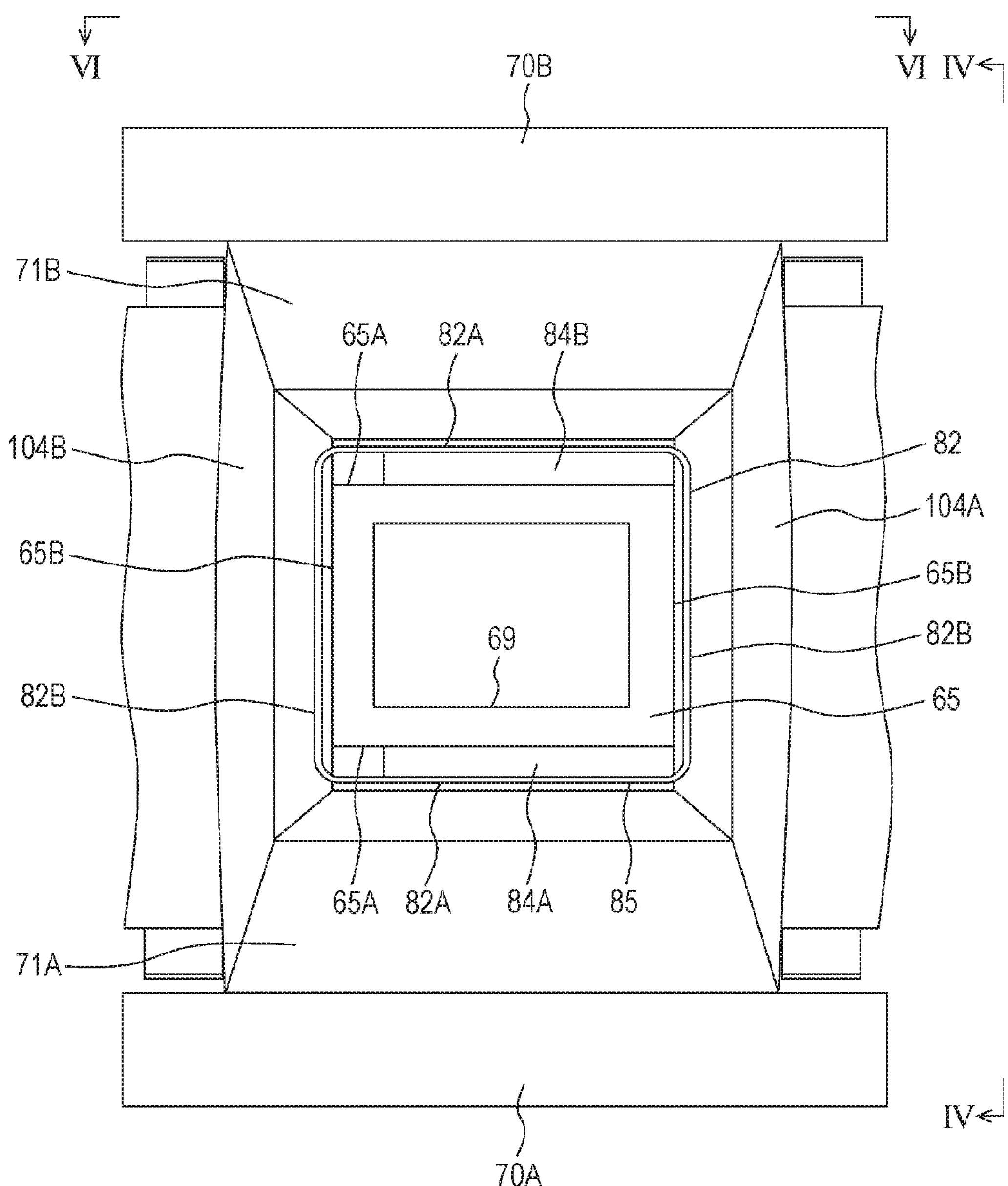
FIG. 5 is a cross sectional view taken along arrows V-V of FIGS. 4 and 6.
Figure 6:
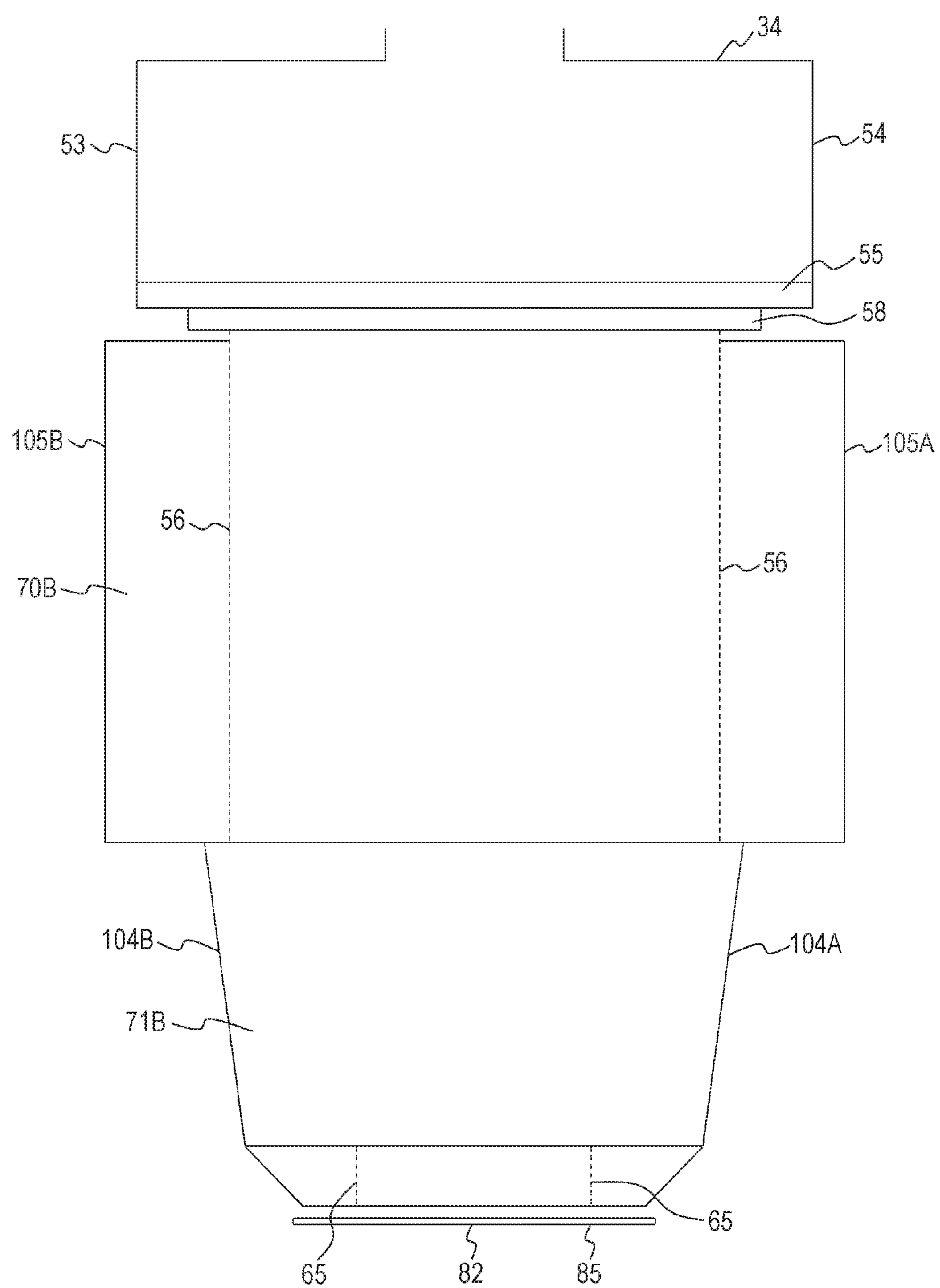
FIG. 6 is a cross sectional view taken along arrows VI-VI of FIG. 5.

The touch sensor apparatuses (first touch sensor apparatuses) 61A and 61B are installed in the middle housing unit 53B. The touch sensor apparatus 61A includes a cover 70A, a pair of cover support apparatuses 72A, a pair of cover support apparatuses 72B, and multiple sensor units 76. Each of the pair of cover support apparatuses 72A and the pair of cover support apparatuses 72B is attached to the back surface of the cover 70A. As illustrated in FIG. 4, one of the cover support apparatuses 72A and one of the cover support apparatuses 72B are disposed away from each other in the direction of the center axis 107, and are attached to one of the support members 60A of the middle housing unit 53B. Although not shown in the drawings, the other of the cover support apparatuses 72A and the other of the cover support apparatuses 72B are also disposed away from each other in the direction of the center axis 107 and are attached to the other of the support members 60A. Accordingly, the cover 70A is held on the middle housing unit 53B with the pair of cover support apparatuses 72A and the pair of cover support apparatuses 72B.

The touch sensor apparatus 61B includes a cover 70B, a pair of cover support apparatuses 72C, a pair of cover support apparatuses 72D, and multiple sensor units 76. Each of the pair of cover support apparatuses 72C and the pair of cover support apparatuses 72D is attached to the back surface of the cover 70B. As illustrated in FIG. 4, one of the cover support apparatuses 72C and one of the cover support apparatuses 72D are disposed away from each other in the direction of the center axis 107, and are attached to one of the support members 60B of the middle housing unit 53B. Although not shown in the drawings, the other of the cover support apparatuses 72C and the other of the cover support apparatuses 72D are also disposed away from each other in the direction of the center axis 107 and are attached to the other of the support members 60B. Accordingly, the cover 70B is held on the middle housing unit 53B with the pair of cover support apparatuses 72C and the pair of cover support apparatuses 72D.

In an area where the middle housing unit 53B exists, the cover 70A and the cover 70B held on the middle housing unit 53B form the other pair of opposing side walls of the irradiation apparatus 34. The cover 70A and the cover 70B are side walls of the irradiation apparatus 34, which face rotary directions of the irradiation apparatus 34. In an area of the irradiation apparatus 34 where the middle housing unit 53B exists, the four side walls formed by the covers 70A, 105A, 70B, and 105B exist.

Figure 7:
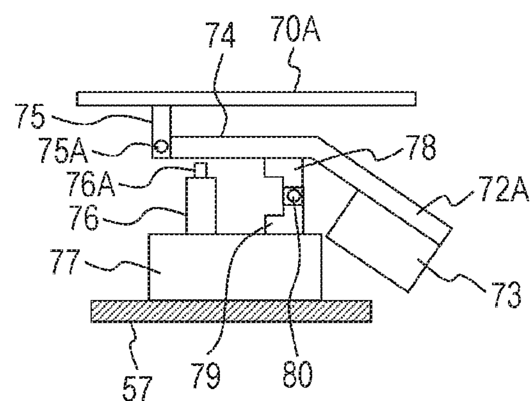
FIG. 7 is an enlarged view illustrating a touch sensor apparatus arranged on a side surface of an irradiation apparatus as illustrated in FIG. 4.
Figure 8:
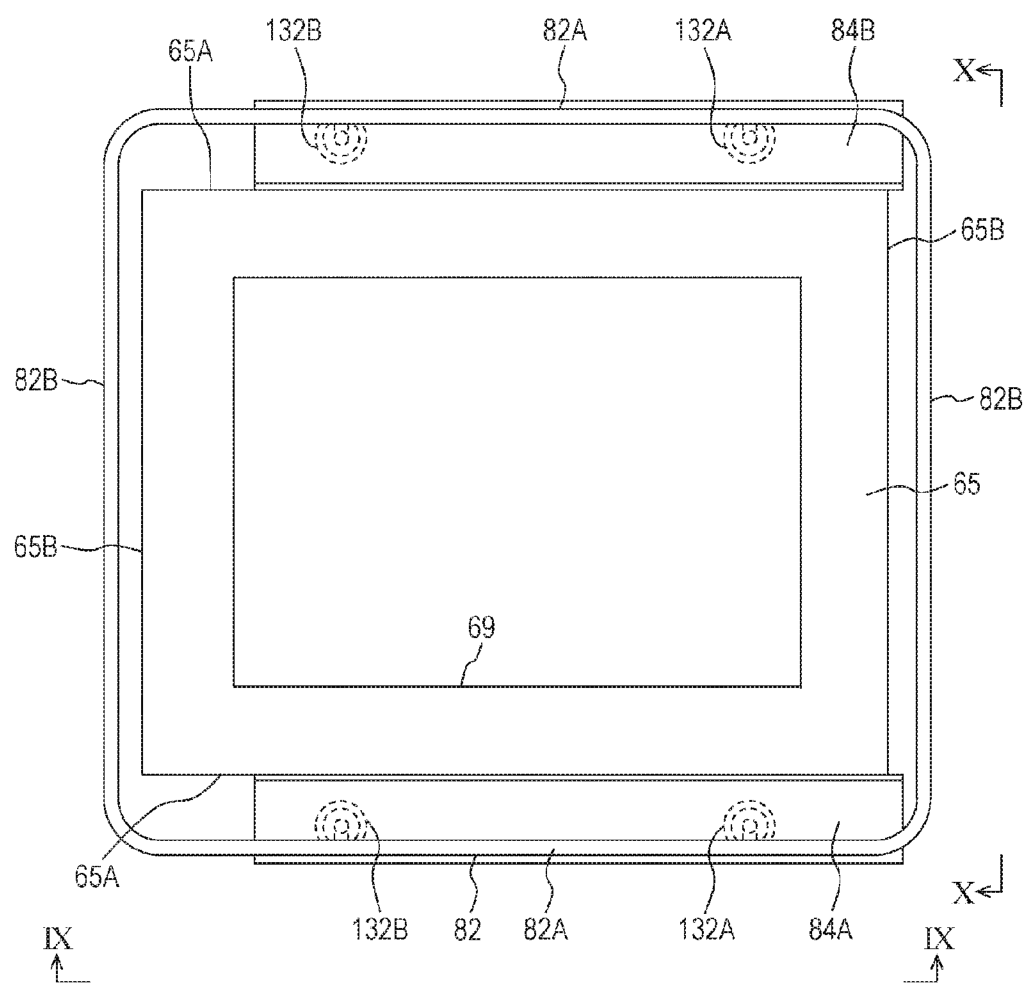
FIG. 8 is an enlarged view illustrating another touch sensor apparatus arranged at a tip of the irradiation apparatus as illustrated in FIG. 4.

The structure of the cover support apparatus 72A will be explained with reference to FIG. 7. The cover support apparatus 72A includes a counter weight 73, a link 74, and a fixing member 77. The link 74 is in a bent shape which is bent to one side. The counter weight 73 is attached to one end portion of the link 74 so as to protrude in a bent direction of the link 74. In the middle between one end portion of the link 74 where the counter weight 73 is attached and the other end portion of the link 74, a protruding portion 78 of the link 74 which is formed on one surface at a bent side is rotatably attached to a support unit 79 attached to the fixing member 79 with a pin (axial member) 80. The link 74 rotatably attached to the support unit 79 of the fixing member 79 is configured such that the one end portion of the link 74 where the counter weight 73 is attached is bent to the side of the fixing member 77.

The other end portion of the link 74 is rotatably attached to a connection unit 75 attached, with a pin 75A, to the back surface of the cover 70A. The fixing member 79 is attached to a single support plate 57 attached to one of the support members 60A of the middle housing unit 53B.

The cover support apparatuses 72B, 72C, and 72D also have the same structure as the cover support apparatus 72A. The cover support apparatuses 72A, 72B, 72C, and 72D are fixed to the fixing member 79 so that the sensor unit 76 having a switch 76A is located between the protruding portion 78 and the pin 75A. The switch 76A faces the link 74 between the protruding portion 78 and the pin 75A.

The connection unit 75 is attached to each of the three positions on the back surface of the cover 70A where the other of the cover support apparatuses 72A and the pair of cover support apparatuses 72B are attached. At the position where this cover support apparatus 72A is attached, one end portion of the link 74 of the other of the cover support apparatuses 72A is rotatably attached, with the pin 75A, to the connection unit 75 attached to the back surface of the cover 70A. Likewise, at the position where the cover support apparatus 72B is attached, one end portion of each of the links 74 of the pair of cover support apparatuses 72B is rotatably attached, with a separate pin 75A, to the connection unit 75 attached to the back surface of the cover 70A.

Further, the fixing member 79 of the other of the cover support apparatuses 72A is attached to the support plate 57 attached to the other of the support members 60A. The fixing members 79 of the pair of cover support apparatuses 72B are separately attached to the support plates 57 attached to the pair of support members 60A of the middle housing unit 53B.

In the touch sensor apparatus 61B, the pair of cover support apparatuses 72C and the pair of cover support apparatuses 72D are rotatably attached, with the pins 75A, to the connection units 75 which one end portion of the link 74 is attached at four locations on the back surface of the cover 70B, so that the pair of cover support apparatuses 72C and the pair of cover support apparatuses 72D are attached to the cover 70B. The fixing member 77 of each of one of the cover support apparatuses 72C and one of the cover support apparatuses 72D is attached to the support plate 57 attached to one of the support members 60B. The fixing member 77 of each of the other of the cover support apparatuses 72C and the other of the cover support apparatuses 72D is attached to the support plate 57 attached to the other of the support members 60B.

As described above, the cover 70A is held on the middle housing unit 53B with the pair of cover support apparatuses 72A and the pair of cover support apparatuses 72B as described above, and the cover 70B is held on the middle housing unit 53B with the pair of cover support apparatuses 72C and the pair of cover support apparatuses 72D as described above.

The touch sensor apparatuses (first touch sensor apparatuses) 61C and 61D are installed in the lower housing unit 53C. The touch sensor apparatus 61C includes a cover 71A, a pair of cover support apparatuses 72E, a pair of cover support apparatuses 72F, and multiple sensor units 76. The cover support apparatuses 72E and 72F have the same configuration as the cover support apparatus 72A. Like the case of the cover support apparatus 72A, the sensor unit 76 having the switch 76A is attached to the fixing member 79 of each of the cover support apparatuses 72E and 72F so that the sensor unit 76 is located between the protruding portion 78 and the pin 75A. The switch 76A faces the link 74 between the protruding portion 78 and the pin 75A. Like the cover support apparatus 72A, each of the pair of cover support apparatuses 72E and the pair of cover support apparatuses 72F is attached to the back surface of the cover 71A. As illustrated in FIG. 4, one of the cover support apparatuses 72E and one of the cover support apparatuses 72F are away from each other in the direction of the center axis 107, and are attached to one of the support members 64A of the lower housing unit 53C. More specifically, the fixing member 79 of the cover support apparatus 72E is attached to the support plate 57 attached to the support member 103A attached to the one of the support members 64A. The fixing member 79 of the cover support apparatus 72F is attached to another support plate 57 attached to the support member 103B attached to the one of the support members 64A. Further, the other of the cover support apparatuses 72E and the other of the cover support apparatuses 72F are away from each other in the direction of the center axis 107 and attached to the other of the support members 64A, not shown, in the same manner. Accordingly, the cover 71A is held on the lower housing unit 53C with the pair of cover support apparatuses 72E and the pair of cover support apparatuses 72F.

The touch sensor apparatus 61D includes a cover 71B, a pair of cover support apparatuses 72G, a pair of cover support apparatuses 72H, and multiple sensor units 76. The cover support apparatuses 72G and 72H have the same configuration as the cover support apparatus 72A. Like the case of the cover support apparatus 72A, the sensor unit 76 having the switch 76A is attached to the fixing member 79 of each of the cover support apparatuses 72G and 72H so that the sensor unit 76 is located between the protruding portion 78 and the pin 75A. The switch 76A faces the link 74 between the protruding portion 78 and the pin 75A. Like the cover support apparatus 72A, each of the pair of cover support apparatuses 72G and the pair of cover support apparatuses 72H is attached to the back surface of the cover 71B. As illustrated in FIG. 4, one of the cover support apparatuses 72G and one of the cover support apparatuses 72H are away from each other in the direction of the center axis 107, and are attached to one of the support members 64B of the lower housing unit 53C. More specifically, the fixing member 79 of the cover support apparatus 72G is attached to the support plate 57 attached to the support member 103C attached to the one of the support members 64B. The fixing member 79 of the cover support apparatus 72H is attached to another support plate 57 attached to the support member 103D attached to the one of the support members 64B. Further, the other of the cover support apparatuses 72G and the other of the cover support apparatuses 72H are away from each other in the direction of the center axis 107 and attached to the other of the support members 64B, not shown, in the same manner. Accordingly, the cover 71B is held on the lower housing unit 53C with the pair of cover support apparatuses 72G and the pair of cover support apparatuses 72H.

In an area where the lower housing unit 53C exists, the cover 71A and the cover 71B held on the lower housing unit 53C form the other pair of opposing side walls of the irradiation apparatus 34. The cover 71A and the cover 71B are side walls of the irradiation apparatus 34, which face rotary directions of the irradiation apparatus 34. In an area of the irradiation apparatus 34 where the lower housing unit 53C exists, the four side walls formed by the covers 71A, 104A, 71B, and 104B exist.

The cover 70A of the touch sensor apparatus 61A, the cover 70B of the touch sensor apparatus 61B, the cover 71A of the touch sensor apparatus 61C, and the cover 71B of the touch sensor apparatus 61D are the side walls of the irradiation apparatus 34, and at the same time, the cover 70A of the touch sensor apparatus 61A, the cover 70B of the touch sensor apparatus 61B, the cover 71A of the touch sensor apparatus 61C, and the cover 71B of the touch sensor apparatus 61D are contact detection units. Further, the cover support apparatuses 72A, 72B, 72C, 72D, 72E, 72F, 72G, and 72H are support apparatuses of the contact detection units. The sensor unit 76 of each of the cover support apparatuses 72A, 72B, 72C, 72D, 72E, 72F, 72G, and 72H is connected to the nozzle control apparatus 83.

The collimator accommodation unit 65 is attached to the lower flange 63 of the lower housing unit 53C, and the collimator accommodation unit 65 which is the tip of the irradiation apparatus 34 has a collimator (not shown) provided therein. The collimator accommodation unit 65 is formed with a rectangular opening portion 69 in which an ion beam passes.

Further, the touch sensor apparatus 85 is located at the tip of the irradiation apparatus 34. The structure of the touch sensor apparatus 85 will be explained with reference to FIG. 8, FIG. 9, FIG. 10, FIG. 11, and FIG. 12.

The touch sensor apparatus (second touch sensor apparatus) 85 includes a contact detection apparatus 82, detection unit support apparatuses 87A and 87B, slide mechanisms 132A and 132B, and touch sensors (touch sensor units) 94A and 94B. The touch sensor apparatus 85 includes not only a pair of slide mechanisms 132A and 132B but also a pair of touch sensors 94A and 94B. The contact detection apparatus 82 includes a pair of round bar-shaped contact detection units 82A and a pair of round bar-shaped contact detection units 82B (see FIG. 8 and FIG. 9). Each of the contact detection units 82A and each of the contact detection units 82B are in parallel with a lower surface (apical surface) 65C of the collimator accommodation unit 65 and are disposed below the lower surface 65C. Each of the pair of contact detection units 82A has a straight line portion occupying most of the portion except both end portions, and these straight line portions are disposed along each of the opposing longer side surfaces 65A of the collimator accommodation unit 65. Each of the pair of contact detection units 82B has a straight line portion occupying most of the portion except both end portions, and these straight line portions are disposed along the other opposing shorter side surfaces 65B of the collimator accommodation unit 65 perpendicular to the side surfaces 65A. In the contact detection apparatus 82, one end portion of each of the pair of contact detection units 82A is coupled with a single contact detection unit 82B, the other end portion of each of these contact detection units 82A is coupled with another contact detection unit 82B, so that a rectangular ring is formed.

A flat plate portion 84Aa of an L-shaped support member (third support member) 84A made by bending a flat plate in a right angle is attached to the collimator accommodation unit 65 while the flat plate portion 84Aa is in contact with one of the side surfaces 65A of the collimator accommodation unit 65. Likewise, an L-shaped support member 84B (fourth support member) made by bending a flat plate in a right angle is attached to the collimator accommodation unit 65 while the L-shaped support member 84B is in contact with the other of the side surfaces 65A of the collimator accommodation unit 65.

The contact detection apparatus 82 is attached to the collimator accommodation unit 65 with the detection unit support apparatuses 87A and 87B. Each of the detection unit support apparatuses 87A and 87B (see FIG. 10) includes support rods 131A and 131B, a support member 88, and coil springs (spring members) 97A and 97B.

The detection unit support apparatus 87A (first detection unit support apparatus) is attached to a support member 84A attached to the collimator accommodation unit 65. In the detection unit support apparatus 87A, support rods (second support members) 131A and 131B are attached to the straight line portion of the contact detection unit 82A, and the support rods (second support members) 131A and 131B separately pass through penetration holes 101 provided at two locations formed in a flat plate portion 84Ab of the support member 84A, and extend toward the collimator accommodation unit 65. The internal diameter of each of the penetration holes 101 is larger than the external diameter of the support rods 131A and 131B, and does not greatly restrict each of the support rods 131A and 131B from moving in a direction perpendicular to the center axis thereof. Each of the support rods 131A and 131B is attached to the plate-shaped support member 88 (first support member) arranged between the flat plate portion 84Ab of the support member 84A and the lower flange 63. One end portion of the support member 88 is attached to the flat plate portion 84Ab of the support member 84A with a single coil spring 97A. More specifically, one end of the coil spring 97A is attached to a pin member 99A engaged, using a screw, with an attachment portion 100A attached to the flat plate portion 84Ab. The other end of the coil spring 97A is attached to a pin member 99B engaged, using a screw, with an attachment portion 100B attached to one end portion of the support member 88. Like the coil spring 97A, the other end portion of the support member 88 is attached to the flat plate portion 84Ab of the support member 84A with another coil spring 97B.

The slide mechanism 132A includes a guide member 90 and a position determination member 92. The guide member 90 is attached to the support member 88 so as to face the flat plate portion 84Ab. The guide member 90 is formed with a circular hole 90A at a flat surface side of the guide member 90 facing the flat plate portion 84Ab, and further, the guide member 90 is formed with a conical hole portion 90C extending from this circular hole 90A to the support member 88. With the formation of the conical hole portion 90C, an inclination surface (guide surface) 90B extending form the inner surface of the circular hole 90A to a point at a side of the support member 88 located on the center line of the circular hole 90A is formed in the guide member 90. A base member 91 formed with the position determination member 92 is attached to the flat plate portion 84Ab. The position determination member 92 is a protruding portion extending from the base member 91 to the support member 88, and is inserted into the circular hole 90A and the conical hole portion 90C. The tip of the position determination member 92 is in a hemispherical shape. The hemisphere which is the tip of the position determination member 92 is in contact with the inclination surface 90B extending to the point thereof.

The slide mechanism 132B has the same structure as the slide mechanism 132A. The guide member 90 of the slide mechanism 132B is attached to the support member 88, and the base member 91 forming the position determination member 92 of the slide mechanism 132B is attached to the flat plate portion 84Ab.

In the slide mechanisms 132A and 132B, the guide member 90 may be attached to the flat plate portion 84Ab, and the position determination member 92 may be attached to the support member 88.

Figure 11:
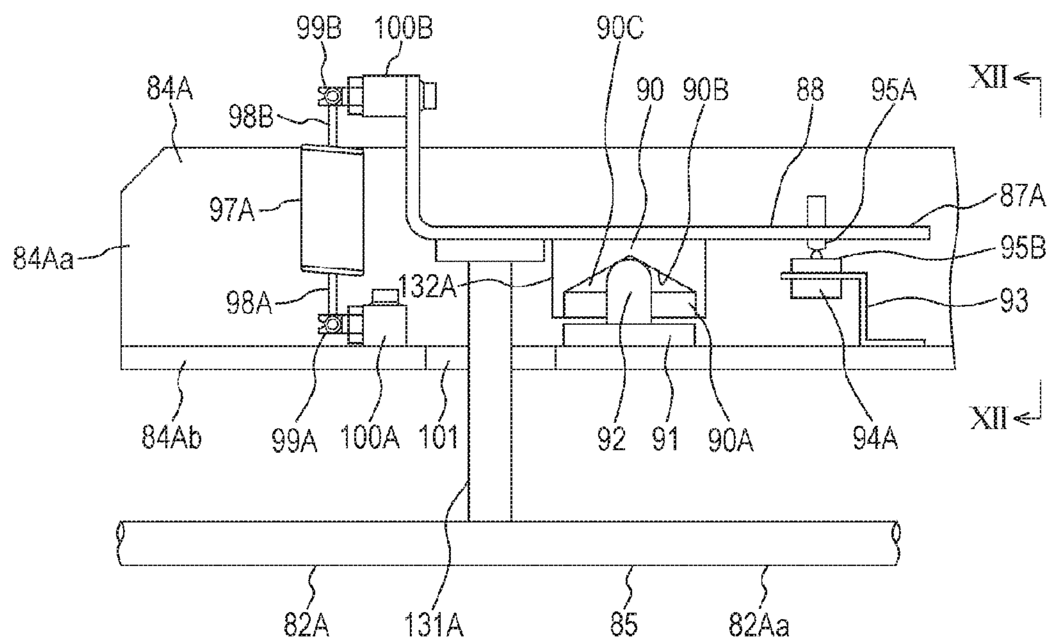
FIG. 11 is an enlarged view of XI portion in FIG. 9.
Figure 12:
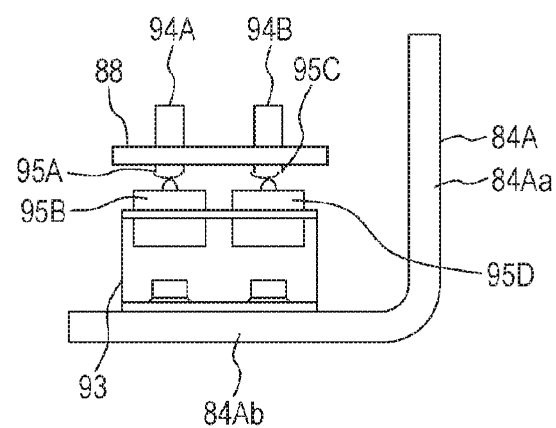
FIG. 12 is a cross sectional view taken along arrows XI-XI of FIG. 11.

The touch sensors 94A and 94B are arranged side by side in proximity to the slide mechanism 132A (see FIG. 11 and FIG. 12). The touch sensor 94A includes sensor units 95A and 95B, and the touch sensor 94B includes sensor units 95C and 95D. The sensor units (first sensor units) 95A and 95C are attached to the support member 88, and the sensor units (second sensor units) 95B and 95D are attached to the support member 93 attached to the flat plate portion 84Ab. The sensor unit 95A faces the sensor unit 95B, and the sensor unit 95C faces the sensor unit 95D. The touch sensor 94A, which is, more specifically, the sensor unit 95A, and the touch sensor 94B, which is, more specifically, the sensor unit 95C, are connected to the nozzle control apparatus 83.

Each of the coil springs 97A and 97B pulls the support member 88 toward the flat plate portion 84Ab of the support member 84A. Therefore, the hemisphere which is the tip of the position determination member 92 is in contact with the entire surface of the inclination surface 90B extending to the point thereof, and is stably held. With such action of the coil springs 97A and 97B, normally, the sensor unit 95A is in contact with the sensor unit 95B, and the sensor unit 95C is in contact with the sensor unit 95D.

The other of the touch sensors 94A is disposed in proximity to the slide mechanism 132B (see FIG. 9), and the touch sensor 94B, not shown, disposed side by side with the touch sensors 94A exists at the side of the touch sensor 94A.

Like the detection unit support apparatus 87A, the detection unit support apparatus 87B (second detection unit support apparatus) (see FIG. 10) is attached to the support member 84B attached to the collimator accommodation unit 65, and the detection unit support apparatus 87B has the same structure as the detection unit support apparatus 87A. Like the detection unit support apparatus 87A, the support member 88 (fourth support member) of the detection unit support apparatus 87B is also attached with a guide member 90 for each of the slide mechanisms 132A and 132B, and a sensor unit 95A for each of the pair of touch sensors 94A, and a sensor unit 95C for each of the pair of touch sensors 94B. The base member 91 of each of the slide mechanisms 132A and 132B for forming the position determination member 92 facing the guide member 90 of each of the slide mechanisms 132A and 132B attached to the support member 88 is attached to the flat plate portion 84Ab of the support member 84B. The sensor unit 95B of each of the pair of touch sensors 94A and the sensor unit 95D of each of the pair of touch sensors 94B are attached to the support member 93 attached to the flat plate portion 84Ab of the support member 84B.

An irradiation method of an ion beam to the affected are of the patient by using the particle beam irradiation apparatus 1 according to the present embodiment will be hereinafter explained. Before the ion beam is irradiated to the affected area, the position of the affected area with respect to the center axis 107 of the irradiation apparatus 34 is determined. In the present embodiment, for example, as described in Japanese Patent Laid-Open No. 2006-239403, X ray CT imaging and position determination of the affected area with rotation of the rotary gantry 27 are carried out.

Before the position determination of the affected area is carried out, the X ray CT imaging of the affected area of the patient 102 is carried out. This X ray CT imaging is carried out before a treatment plan for the patient 102 is planned. Tomographic image information obtained from the X ray CT imaging (hereinafter referred to as reference tomographic image information) is stored to the memory 111 of the central control apparatus 109.

Further, before the position determination of the affected area is carried out before the irradiation of the ion beam, the bed 48 of the treatment bed 39 on which the patient 102 lies to a predetermined position in the treatment cage 43 in the treatment chamber 40. The movement of the bed 48 is performed when an operator inputs a bed operation command for moving the bed 48 to a predetermined position within a control chamber (not shown) by using an input apparatus (not shown) connected to the CPU 110 provided on an operation board (not shown) installed in this control chamber. A control command that is output from the CPU 110 on the basis of this bed operation command is input into the bed control apparatus 115. The bed control apparatus 115 drives the X direction drive mechanism 49, the Y direction drive mechanism 50, the upper and lower direction drive mechanism 51, and the rotary drive mechanism 52 on the basis of this control command, and automatically moves the bed 48 to a predetermined position.

Thereafter, in order to obtain current tomographic image information required for determining the position of the affected area, the X ray CT imaging with rotation of the rotary gantry 27 is performed. An X ray tube (not shown) and an X ray transmission image imaging apparatus (not shown) provided in the irradiation apparatus 34 are used for the X ray CT imaging. When an operator inputs an X ray irradiation command into the CPU 110 by using the input apparatus in the control chamber, the X ray irradiation control command that is output from the CPU 110 is output to an X ray source control apparatus (not shown) and an imaging unit movement control apparatus (not shown). As described in Japanese Patent Laid-Open No. 2006-239403, the X ray source control apparatus drives an X ray source drive apparatus (not shown) provided in the irradiation apparatus 34 and having the X ray tube attached thereto, and moves the X ray tube to the center axis 107. The imaging unit movement control apparatus drives the imaging unit movement apparatus having the X ray detection apparatus attached thereto, and moves the X ray detection apparatus to the position of the center axis 107 below the bed 48 and facing the X ray tube.

The X ray source control apparatus discharges an X ray from the X ray tube on the basis of the X ray irradiation control command. When the operator inputs a rotary command into the CPU 110 by using the input apparatus, rotary control command that is output from the CPU 110 is output to the gantry control apparatus 112. At this occasion, the gantry control apparatus 112 drives the rotary apparatus 44, and rotates, about the center line 28A, the rotary gantry 27, for example, from 0 degrees to 185 degrees in a clockwise direction in FIG. 3. With the rotation of the rotary gantry 27, the X ray tube attached to the irradiation apparatus 34 and emitting X ray and the X ray detection apparatus rotate around the patient 102 who lies on the bed 48. Accordingly, the X ray is irradiated to the affected area of the patient 102. The X ray discharged from the X ray tube is transmitted through the affected area and the like of the patient 102, and is detected by the X ray detection apparatus. The X ray detection apparatus outputs many X ray detection signals in accordance with the detection of the X ray having been transmitted therethrough. These X ray detection signals are input into an image information generation apparatus (not shown). This image information generation apparatus receives a measurement value of a rotation angle of the rotary gantry 27 detected by the angle detection device 45.

When the rotary gantry 27 rotates in the clockwise direction to the 185 degrees, i.e., when the center axis 107 of the irradiation apparatus 34 reaches the position of 185 degrees, the gantry control apparatus 112 receiving the angle detection signal of the angle detection device 45 outputs a rotary stop control command to the rotary apparatus 44, and stops driving of the rotary apparatus 44. At this occasion, the rotation of the rotary gantry 27 is also stopped, and stops the discharge of the X ray from the X ray tube. Thereafter, the rotary gantry control apparatus 113 rotates the rotary apparatus 44 backward. When the rotary gantry 27 rotates in a counterclockwise direction in FIG. 3, and the center axis 107 of the irradiation apparatus 34 reaches the position of 180 degrees, the rotary gantry control apparatus 113 stops the rotary apparatus 44. Then, the rotary gantry control apparatus 113 drives the rotary apparatus 44 again to rotate the rotary gantry 27 in the clockwise direction from 180 degrees to 5 degrees. During the rotation of this rotary gantry 27, the X ray is discharged from the X ray tube, and this X ray is irradiated to the affected area of the patient 102 on the bed 48. The X ray having been transmitted through the affected area is detected by the X ray detection apparatus, and the rotation angle of the rotary gantry 27 is also detected by the angle detection device 45.

As described above, when the X ray tube discharging the X ray and the X ray detection apparatus are rotated around the patient 102 lying on the bed 48, this means that the X ray CT is performed on the patient 102 in a range of 360 degrees.

As described in Japanese Patent Laid-Open No. 2006-239403, the image information generation apparatus generates current tomographic image information about the affected area and the like of the patient 102 on the basis of the X ray detection signals that are output from the X ray detection apparatus and the rotation angle of the rotary gantry 27 detected by the angle detection device 45.

In case the irradiation apparatus 34 comes into contact with the bed 48 or the patient 102 lying on the bed 48 because of the movement of the bed 48 before the X ray tube discharging the X ray is rotated with the rotation of the rotary gantry 27 in order to generate the current tomographic image information, it is necessary to stop the rotation of the irradiation apparatus 34 in view of the safety of the patient 102. The rotation stop of the irradiation apparatus 34 is performed on the basis of a contact signal that is output from the touch sensor apparatuses 61A, 61B, 61C, or 61D, or the touch sensor apparatuses 65 or 65.

First, a detection of a contact between the irradiation apparatus 34 and the bed 48 or the patient 102 lying on the bed 48 with the touch sensor apparatuses 61A, 61B, 61C, and 61D will be explained. Since the touch sensor apparatuses 61A, 61B, 61C, and 61D have the same function for detecting the contact, the detection of the contact with the touch sensor apparatus 61D will be hereinafter explained.

Before the X ray tube discharging the X ray is rotated with the rotation of the rotary gantry 27 in order to generate current tomographic image information, it is necessary to move the bed 48 to a predetermined position within the treatment cage 43 as described above. In the movement of the bed 48 on which the patient 102 lies, it is necessary to cause the patient 102 and the bed 48 to be located at an inner side than the track along which the tip of the irradiation apparatus 34 rotates about the center line 28A so that the bed 48 or the patient 102 does not come into contact with the rotating irradiation apparatus 34. However, suppose a case where an abnormality occurs in the bed control apparatus 115 and the like, and the patient 102 and the bed 48 are located at a position outside of the track.

Figure 3:
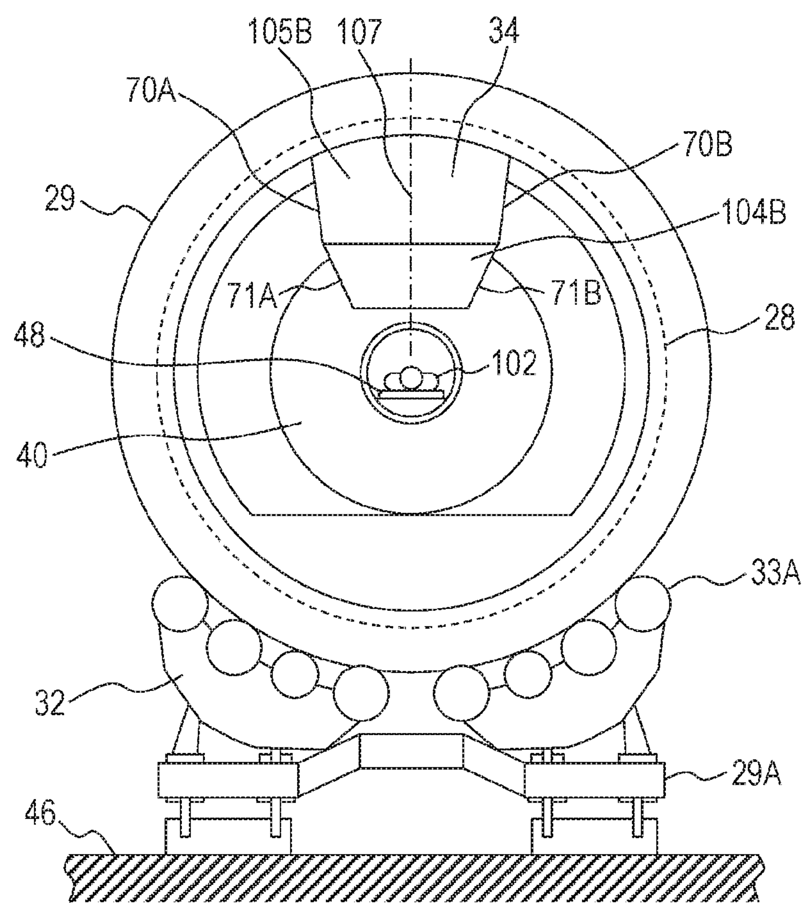
FIG. 3 is a cross sectional view taken along arrows of FIG. 2.

Thereafter, as described above, the rotary gantry 27 is rotated, and the irradiation apparatus 34 is rotated while the X ray is discharged from the X ray tube (for example, the irradiation apparatus 34 is rotated in the clockwise direction in FIG. 3). Eventually, the rotating irradiation apparatus 34 comes into contact with the bed 48 or the patient 102, and for example, this contact is considered to be detected by the touch sensor apparatus 61D installed in the irradiation apparatus 34. In this case, the cover 71B of the touch sensor apparatus 61D comes into contact with the bed 48 or the patient 102 in accordance with the rotation of the irradiation apparatus 34. With this contact, the cover 71B moves toward the lower housing unit 53C.

Figure 14:
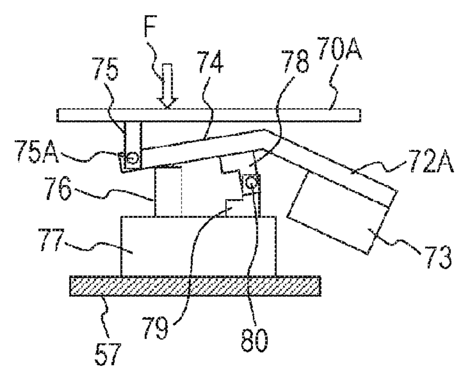
FIG. 14 is an explanatory diagram illustrating a state when an interference of an irradiation apparatus is detected by the touch sensor apparatus as illustrated in FIG. 7.

When the cover 71B moves toward the lower housing unit 53C, the link 74 of each of the pair of cover support members 72G and 72H of the touch sensor apparatus 61D is rotated about a pin 80, and the end portion of each link 74 at the side of the connection unit 75 moves toward the fixing member 77 (see FIG. 14). As a result, the switch 76A of the sensor unit 76 attached to the fixing member 77 of each of the cover support members 72G and 72H is pushed by the end portion of the link 74 at the side of the connection unit 75, and accordingly, contact signals are output from these sensor units 76. Each of the output contact signals is input into the nozzle control apparatus 83, and is displayed as a warning on a display apparatus provided on a control board in a control chamber. Further, each of the output contact signals is input into the gantry control apparatus 113 and the X ray source control apparatus from the nozzle control apparatus 83. The gantry control apparatus 113 having received the contact signal stops the rotary apparatus 44 and stops the rotation of the rotary gantry 27. The X ray source control apparatus having received the contact signal stops the discharge of the X ray from the X ray tube.

Thereafter, the gantry control apparatus 113 rotates the rotary apparatus 44 backward. The rotary gantry 27 is also rotated backward, and the cover 71B of the touch sensor apparatus 61D is moved away from the bed 48 or the patient 102. The cover 71B is returned back to the position before the contact. Accordingly, the link 74 of each of the cover support members 72G and 72H returns back from the state as illustrated in FIG. 14 to the state as illustrated in FIG. 7, and the output of the contact signal from the sensor unit 76 of each of the cover support members 72G and 72H is stopped.

When the cause of making the cover 71B to be in contact with the bed 48 or the patient 102 is eliminated (for example, completion of repair of the bed control apparatus 115 in an abnormal state), and the bed 48 is located at an inner side than the track along which the tip of the irradiation apparatus 34 rotates about the center line 28A, the rotary gantry 27 is rotated while the X ray is discharged from the X ray tube, and the X ray is irradiated from around the patient 102 to the affected area of the patient 102 who lies on the bed 48.

When the rotary gantry 27 is rotating in the clockwise direction, and the cover 70B of the touch sensor apparatus 61B comes into contact with the bed 48 or the patient 102, the sensor unit 76 provided on each of the pair of cover support members 72C and 72D of the touch sensor apparatus 61B outputs a contact signal.

When the cover 71A of the touch sensor apparatus 61C comes into contact with the bed 48 or the patient 102 while the rotary gantry 27 is rotating in the counterclockwise direction, the sensor unit 76 provided in each of the pair of cover support members 72E and 72F of the touch sensor apparatus 61C outputs a contact signal. Further, when the cover 70A of the touch sensor apparatus 61A comes into contact with the bed 48 or the patient 102 while the rotary gantry 27 is rotating in the counterclockwise direction, the sensor unit 76 provided in each of the pair of cover support members 72A and 72B of the touch sensor apparatus 61A outputs a contact signal.

Subsequently, a detection of a contact between the irradiation apparatus 34 and the bed 48 or the patient 102 who lies on the bed 48 with the touch sensor apparatus 85 will be explained.

As described above, it is assumed that, in the movement of the bed 48 to a predetermined position in the treatment cage 43 before the X ray tube discharging the X ray is rotated, an abnormality occurs in the bed control apparatus 115 and the like, and the patient 102 and the bed 48 are located on that track. Then, it is assumed that, when the irradiation apparatus 34 is rotated in the clockwise direction in FIG. 3 while the X ray is discharged from the X ray tube, the contact detection apparatus 82 of the touch sensor apparatus 85 (for example, the contact detection unit 82A located at the support member 84B) comes into contact with the bed 48 or the patient 102.

Figure 9:
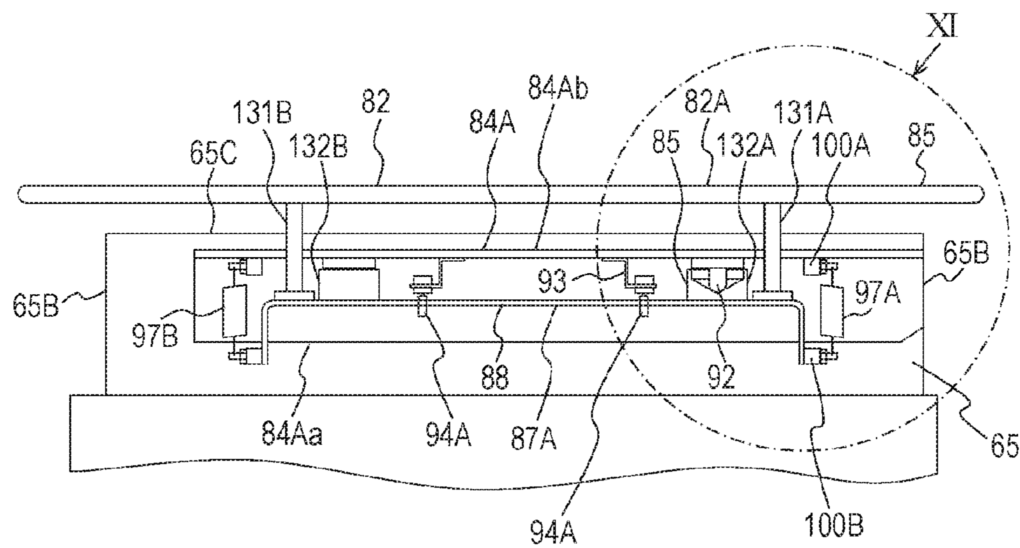
FIG. 9 is a cross sectional view taken along arrows IX-IX of FIG. 8.
Figure 10:
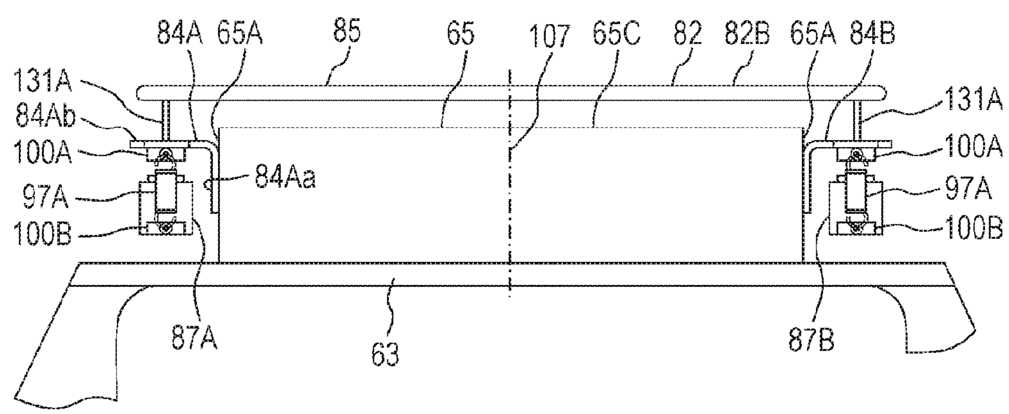
FIG. 10 is a cross sectional view taken along arrows X-X of FIG. 8.

When the bed 48 or the patient 102 comes into contact with the contact detection unit 82A, the support rods 131A and 131B of the detection unit support apparatus 87B attached to the support member 84B move toward the lower flange 63 of the lower housing unit 53C. The structure of the detection unit support apparatus 87B is the same as the structure of the detection unit support apparatus 87A. Therefore, the actions of the detection unit support apparatus 87B will be explained by using the detection unit support apparatus 87A as illustrated in FIG. 9 and FIG. 11. Further, operation of each of the slide mechanisms 132A and 132B, the pair of touch sensors 94A, and the pair of touch sensors 94B provided at the support member 84B in accordance with the action of the detection unit support apparatus 87B will be explained with reference to FIG. 9 and FIG. 11.

The support rods 131A and 131B of the detection unit support apparatus 87B move toward the lower flange 63 of the lower housing unit 53C, the support rods 131A and 131B are pulled by the coil springs 97A and 97B toward the flat plate portion 84Ab of the support member 84B. The support member 88 of the detection unit support apparatus 87B moves toward the lower flange 63 against the pulling force of each of the coil springs 97A and 97B. As a result, the sensor unit 95A of each touch sensor 94A and the sensor unit 95C of each touch sensor 94B attached to this support member 88 are attached to the support member 93 installed on the flat plate portion 84Ab of the support member 84B, and are away from the sensor unit 95B of each touch sensor 94A and the sensor unit 95D of each touch sensor 94B which are in contact with these sensor units. When the sensor unit 95A and the sensor unit 95B are in a contact state, the sensor units 95A and 95B are in an energized state, but when the sensor unit 95A and the sensor unit 95B are in a non-contact state, these sensor units are in a non-energized state. When the sensor unit 95C and the sensor unit 95D are in a contact state, the sensor units 95C and 95D are in an energized state, but when the sensor unit 95C and the sensor unit 95D are in a non-contact state, these sensor units are in a non-energized state.

When the sensor unit 95A and the sensor unit 95B are in a non-contact state, and the energized state between these sensor units is stopped, an electric current measured by an ammeter (not shown) connected to the sensor unit 95A becomes zero. Likewise, when the energized state between the sensor unit 95C and the sensor unit 95D is stopped, an electric current measured by an ammeter (not shown) connected to the sensor unit 95C becomes zero. A signal of an electric current measurement value "0" that is output from the ammeter, i.e., a contact signal, is displayed as a warning on the display apparatus provided on the control board. Further, the signal is output via the nozzle control apparatus 83 to the gantry control apparatus 113 and the X ray source control apparatus. The gantry control apparatus 113 having received the contact signal stops the rotary apparatus 44 and stops the rotation of the rotary gantry 27. The X ray source control apparatus having received the contact signal stops the discharge of the X ray from the X ray tube.

Thereafter, the gantry control apparatus 113 rotates the rotary apparatus 44 backward, and rotates the rotary gantry 27 backward. The contact detection unit 82A is moved away from the bed 48 or the patient 102 having come into contact therewith. At this occasion, the support member 88 of the detection unit support apparatus 87B moves toward the flat plate portion 84Ab of the support member 84B in accordance with the pulling force of each of the coil springs 97A and 97B.

Even when the contact detection unit 82A comes into contact with the bed 48 or the patient 102, and the support member 88 of the detection unit support apparatus 87B is moving toward the lower flange 63, the position determination member 92 in each of the slide mechanisms 132A and 132B is located in the circular hole 90A and the conical hole portion 90C of the guide member 90 at all times. Therefore, when the support member 88 moves toward the flat plate portion 84Ab of the support member 84B with the action of the coil springs 97A and 97B as described above, the inclination surface 90B of the conical hole portion 90C comes into contact with the hemispheric tip of the position determination member 92. The support member 88 of the detection unit support apparatus 87B is pulled by the coil springs 97A and 97B, and accordingly, the inclination surface 90B comes into contact with and slides on the hemispheric tip of the position determination member 92, and the guide member 90 of each of the slide mechanisms 132A and 132B moves until the center axis of the guide member 90 matches the center axis of the position determination member 92. When the center axis of the guide member 90 matches the center axis of the position determination member 92, the entire periphery of the position determination member 92 comes into contact with the inclination surface 90B of the conical hole portion 90C, and the movement of the guide member 90 is stopped, and the sensor unit 95A of each touch sensor 94A attached to the support member 88 comes into contact with the sensor unit 95B. The sensor unit 95C of each touch sensor 94B attached to the support member 88 comes into contact with the sensor unit 95D. The sensor unit 95A, the sensor unit 95B, the sensor unit 95C, and the sensor unit 95D come into an energized state.

When the cause of making the contact detection unit 82A of the touch sensor apparatus 85 explained above to be in contact with the bed 48 or the patient 102 is eliminated (for example, completion of repair of the bed control apparatus 115 in an abnormal state), and the bed 48 is located at an inner side than the track along which the tip of the irradiation apparatus 34 rotates about the center line 28A, the X ray discharged from the X ray tube is irradiated from around the patient 102 to the affected area of the patient 102 who lies on the bed 48 for current tomographic image information generation.

Hereinafter, an action of the counter weight 73 provided in the cover support apparatus 72A and the like will be explained. It is assumed that the rotary gantry 27 rotates 90 degrees, and the center axis 107 of the irradiation apparatus 34 becomes horizontal (see FIG. 13). The polarization electromagnet 24 is located at the right side in FIG. 13. In this state, the weight of the cover 70B located above is applied to the end portion of the link 74 of the cover support apparatus 72C at side of the pin 75A, and therefore, the end portion of the link 74 at the side of the pin 75A is pressed down, and the switch 76A of the sensor unit 76 attached to the cover support apparatus 72C is pressed by the end portion of the link 74. As a result, even though the cover 70B is not in contact with the bed 48 or the patient 102, a contact signal is output from the sensor unit 76. The weight of the cover 70A located below is applied to the end portion of the link 74 of the cover support apparatus 72A at the side of the pin 75A, and therefore, the end portion of the link 74 at the side of the pin 75A moves to the lower side, and the switch 76A of the sensor unit 76 attached to the cover support apparatus 72A is moved away from the link 74. As a result, even if the bed 48 or the patient 102 comes into contact with the cover 70A, the switch 76A may not be activated. In a case where the switch 76A is not activated, a contact signal may not be output from the sensor unit 76 even if the cover 70A comes into contact with the bed 48 or the patient 102 comes into contact with the cover 70A.

Figure 13:
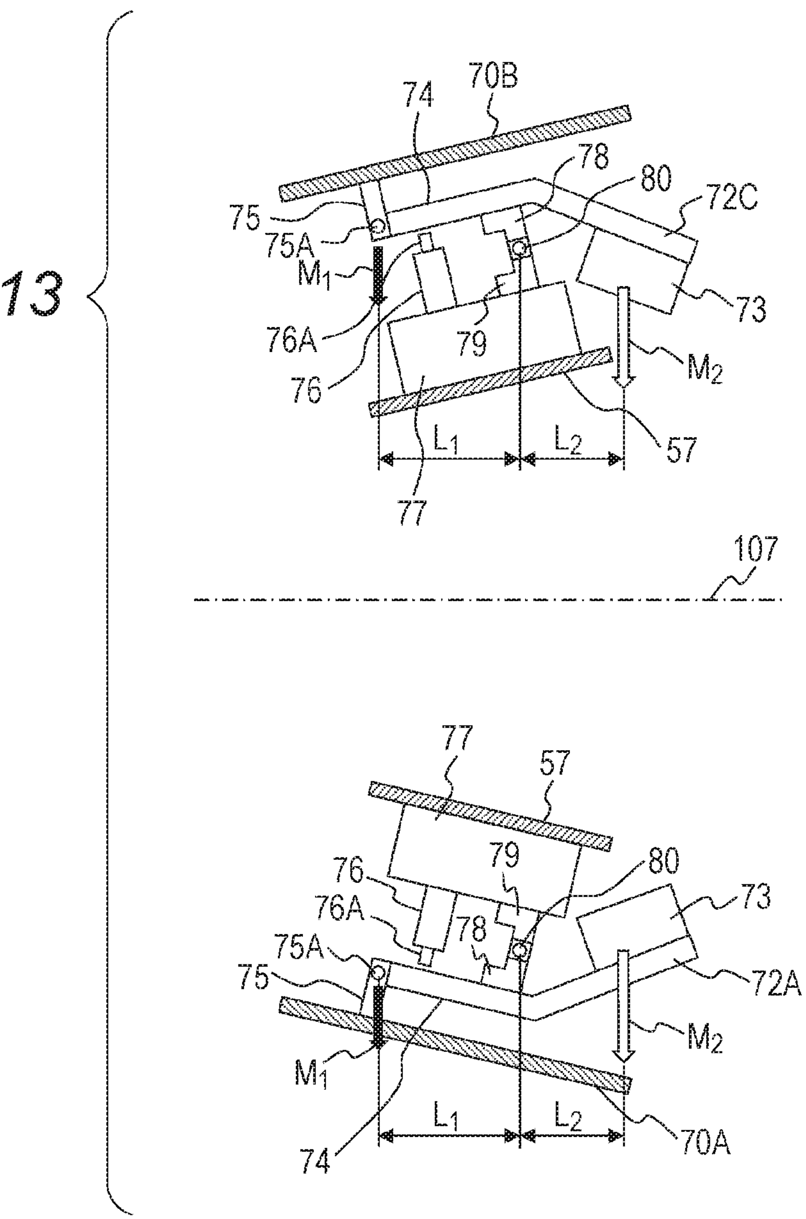
FIG. 13 is an explanatory diagram illustrating an effect of a weight in a touch sensor apparatus as illustrated in FIG. 7 when a center axis of the irradiation apparatus is in a state of facing a horizontal direction.

The counter weight 73 attached to each cover support apparatus solves such problems. As illustrated in FIG. 13, the cover 70B located above is attached with the pair of cover support apparatuses 72C and the pair of cover support apparatuses 72D, so that a weight $W_1$ of the cover 70B is supported by the four cover support apparatuses. Therefore, at one of the cover support apparatuses 72C, a weight $M_1$ applied by the cover 70B to the end portion of the link 74 coupled to the connection unit 75 with the pin 75A is $W_1/4$. A weight of the counter weight 73 provided on the cover support apparatus 72C is $M_2$. In a state in which the center axis 107 of the irradiation apparatus 34 is horizontal (FIG. 13), a distance between the pin 80 and the pin 75A is defined as $L_1$, and a distance between the pin 80 and the barycenter of the counter weight 73 is defined as $L_2$. The weight $M_2$ of the counter weight 73 is preselected so as to satisfy $M_1*L_1=M_2*L_2$. The weight of each counter weight 73 provided in the pair of cover support apparatuses 72D and the other of the cover support apparatuses 72C attached to the cover 70B is also configured to be $M_2$. As a result, when the center axis 107 of the irradiation apparatus 34 is in the horizontal state, the weight of the cover 70B applied to each of the pair of cover support apparatuses 72C and the pair of cover support apparatuses 72D attached to the cover 70B is cancelled by the weight of the counter weight 73 of each cover support apparatus, and the switch 76A of the sensor unit 76 provided on each of the cover support apparatuses 72C and 72D can be prevented from being activated by the weight of the cover 70B.

As illustrated in FIG. 13, the cover 70A located below is attached with the pair of cover support apparatuses 72A and the pair of cover support apparatuses 72B, and the weight $W_1$ of the cover 70A is supported by the four cover support apparatuses. Therefore, the weight $M_2$ of the counter weight 73 of the cover support apparatus 72A is preselected so as to satisfy $M_1*L_1=M_2*L_2$. The weight of each counter weight 73 provided in the pair of cover support apparatuses 72B and the other of the cover support apparatuses 72A attached to the cover 70A is also configured to be $M_2$. As a result, when the center axis 107 of the irradiation apparatus 34 is in the horizontal state, the weight of the cover 70A applied to each of the pair of cover support apparatuses 72A and the pair of cover support apparatuses 72B attached to the cover 70A is cancelled by the weight of the counter weight 73 of each cover support apparatus, and this can prevent the switch 76A of the sensor unit 76 provided on each of the cover support apparatuses 72A and 72B from failing to be activated when the cover 70A comes into contact with the bed 48 or the patient 102.

In the state of FIG. 13, the counter weight 73 provided in each of the cover support apparatuses 72G and 72H attached to the cover 71B located above works in the same manner as the counter weight 73 provided in each of the cover support apparatuses 72C and 72D. The counter weight 73 provided on each of the cover support apparatuses 72E and 72F attached to the cover 71A located below works in the same manner as the counter weight 73 provided on each of the cover support apparatuses 72A and 72B.

It is assumed that the rotary gantry 27 rotates 270 degrees, and the center axis 107 of the irradiation apparatus 34 becomes horizontal (see FIG. 13). The polarization electromagnet 24 is located at the left side in FIG. 13. The counter weight 73 attached to each of the cover support apparatuses 72A and 72B attached to the cover 70A located above and the cover support apparatuses 72E and 72F attached to the cover 71A located above works in the same manner as each counter weight 73 attached to each of the cover support apparatuses 72C and 72D when the rotary gantry 27 rotates 90 degrees. The counter weight 73 attached to each of the cover support apparatuses 72C and 72D attached to the cover 703 located below and the cover support apparatuses 72G and 72H attached to the cover 71B located below works in the same manner as each counter weight 73 attached to each of the cover support apparatuses 72A and 72B when the rotary gantry 27 rotates 90 degrees.

Figure 15:
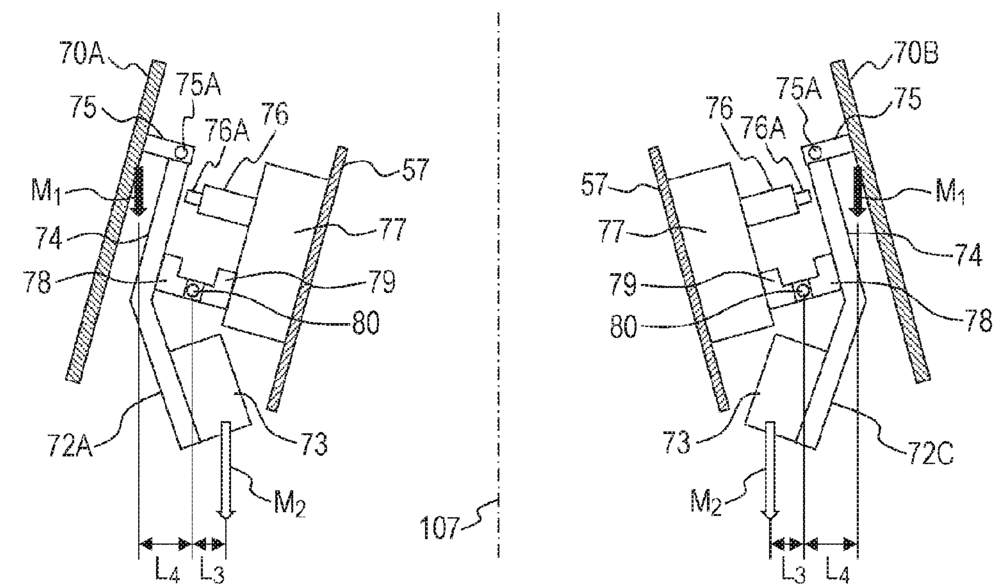
FIG. 15 is an explanatory diagram illustrating an effect of a weight in the touch sensor apparatus as illustrated in FIG. 7 when the center axis of the irradiation apparatus is in a state of being perpendicular to a horizontal direction.

It is assumed that the rotary gantry 27 rotates 180 degrees, and the center axis 107 of the irradiation apparatus 34 becomes perpendicular to the floor surface 46 (see FIG. 15). The polarization electromagnet 24 is located at the lower side in FIG. 15. A distance between an attachment point of the cover 70A and the connection unit 75 and the pin 75A of the cover support apparatus 72A and a distance between an attachment point of the cover 70B and the connection unit 75 and the pin 75A of the cover support apparatus 72C are $L_4$. A distance between the pin 75A of the cover support apparatus 72A and the barycenter of the counter weight 73 of the cover support apparatus 72A and a distance between the pin 75A of the cover support apparatus 72C and the barycenter of the counter weight 73 of the cover support apparatus 72C are $L_3$. A weight applied by the cover 70A to an attachment point of the cover 70A and the connection unit 75 and a weight applied by the cover 70B to an attachment point of the cover 70B and the connection unit 75 are $M_1$. Therefore, with the cover support apparatuses 72A and 72C, $M_1*L_1=M_2*L_2$ is satisfied, and the weight $M_1$ applied to the attachment point of the cover 70A and the connection unit 75 rotating the end portion of the pin 75A of the link 74 of the cover support apparatus 72A to the side of the fixing member 77 is cancelled by the weight $M_2$ of the counter weight 73 of the cover support apparatus 72A. The weight $M_1$ applied to the attachment point of the cover 70B and the connection unit 75 rotating the end portion of the pin 75A of the link 74 of the cover support apparatus 72C to the side of the fixing member 77 is cancelled by the weight $M_2$ of the counter weight 73 of the cover support apparatus 72C. The function of the counter weight 73 of each of the cover support apparatuses 72A and 72C is also achieved by the counter weight 73 of each of the cover support apparatus 72B attached to the cover 70A, the cover support apparatus 72D attached to the cover 70B, the cover support apparatuses 72E and 72F attached to the cover 71A, and the cover support apparatus 72G and 72H attached to the cover 71B.

In contrast to the state of FIG. 15, it is assumed that the rotation angle of the rotary gantry 27 is 0 degrees, the center axis 107 of the irradiation apparatus 34 is perpendicular to the floor surface 46, and the polarization electromagnet 24 is located at the upper side in FIG. 15. At this occasion, in the cover support apparatuses 72A and 72C, $M_1*L_1=M_2*L_2$ is satisfied. The weight $M_1$ applied to the attachment point of the cover 70A and the connection unit 75 acting in a direction in which the end portion of the pin 75A of the link 74 of the cover support apparatus 72A is moved away from the fixing member 77 is cancelled by the weight $M_2$ of the counter weight 73 of the cover support apparatus 72A. The weight $M_1$ applied to the attachment point of the cover 70B and the connection unit 75 acting in a direction in which the end portion of the pin 75A of the link 74 of the cover support apparatus 72C is moved away from the fixing member 77 is cancelled by the weight $M_2$ of the counter weight 73 of the cover support apparatus 72C. The function of the counter weight 73 of each of the cover support apparatuses 72A and 72C generated when the rotation angle of the rotary gantry 27 is zero degrees is also achieved by the counter weight 73 of each of the cover support apparatus 72B attached to the cover 70A, the cover support apparatus 72D attached to the cover 70B, the cover support apparatuses 72E and 72F attached to the cover 71A, and the cover support apparatus 72G and 72H attached to the cover 71B.

When the irradiation apparatus 34 does not come into contact with the bed 48 or the patient 102 in a case where the X ray tube discharging the X ray is rotated around the patient 102 on the bed 48 in order to generate the current tomographic image information, or when the covers 70A, 70B, 71A, and 71B and the contact detection unit 82A come into contact with the bed 48 or the patient 102, and this cause of the contact is eliminated, and the X ray tube discharging the X ray is rotated around the patient 102 on the bed 48, the current tomographic image information about the affected area of the patient 102 is generated as described above.

As described in Japanese Patent Laid-Open No. 2006-239403, the position determination data generation apparatus (not shown) calculates the amount of movement of the bed 48 and the rotation angle of the bed 48 in an X direction and a Y direction which are position determination data in the X-Y plane, and calculates the amount of movement of the bed 48 in a Z direction which is the position determination data in the X-Z plane (upper and lower direction), on the basis of the current tomographic image information received from the image information generation apparatus. Each of the amounts of movements of the bed 48 and the rotation angle of the bed 48 in the X direction, the Y direction, and the Z direction thus calculated are input into the CPU 110, and stored to the memory 111. The CPU 110 outputs each piece of information about each of the amounts of movements of the bed 48 and the rotation angle of the bed 48 in the X direction, the Y direction, and the Z direction to the bed control apparatus 115. The bed control apparatus 115 drives each of the X direction drive mechanism 49, the Y direction drive mechanism 50, the upper and lower direction drive mechanism 51, and the rotary drive mechanism 52 on the basis of the received information to move the bed 48 to a predetermined position, and determines the position of the affected area with respect to the irradiation apparatus 34.

After the position of the affected area has been determined, the ion beam is irradiated to the affected area. An overview of the ion beam irradiation to the affected area will be explained. When the ion beam is irradiated from the irradiation apparatus 34 to the affected area, the X ray tube is moved in a direction perpendicular to the center axis of the irradiation apparatus 34 to a position where the irradiated ion beam is not shielded.

The rotary gantry 27 is rotated by driving the rotary apparatus 44 with the gantry control apparatus 113, so that the center axis 107 of the irradiation apparatus 34 matches the irradiation direction of the ion beam with respect to the affected area. Ions (for example, protons) generated by an ion source are accelerated by the linear accelerator 14, and a proton ion beam (hereinafter referred to as an ion beam) emitted from the linear accelerator 14 passes through the injector 5 and is incident upon the circular beam duct 4 of the synchrotron accelerator 3. The ion beam circulating in the beam duct 4 is accelerated by the radiofrequency acceleration cavity 8 to an energy corresponding to one of the layers of the affected area onto which the ion beam is irradiated.

The scan control apparatus 114 having received a control command from the CPU 110 controls the scan electromagnets 35 and 36, so that the irradiation position of the ion beam in that layer matches the target irradiation position. The acceleration device and transport system control apparatus 112 having received the control command from the CPU 110 closes the open/close switch 12 of the radiofrequency application apparatus 9. The radiofrequency voltage from the radiofrequency power supply 11 is applied to the ion beam circulating from the extraction radiofrequency electrode 10, and the circulating ion beam is emitted from synchrotron accelerator 3 via the septum electromagnet 13 to the beam path 16.

The emitted ion beam passes through the beam path 21 and reaches the irradiation apparatus 34, and the ion beam is irradiated to the target irradiation position in the layer, of which position has been determined, with the scan electromagnets 35 and 36. Thereafter, the ion beam is irradiated to all the irradiation positions in that layer, and further, the ion beam is irradiated to all the layers in the affected area. When the irradiation of the ion beam for all the layers have been finished, the irradiation of the ion beam to the affected area is finished.

The present embodiment can obtain the following effects.

When the bed 48 on which the patient 102 is lying is moved to a predetermined position in accordance with automatic control with the bed control apparatus 115, it is assumed that an abnormal state occurs, and the bed 48 is located at an outer side than the track along which the tip of the irradiation apparatus is rotating. In a case where the irradiation apparatus 34 rotates in the clockwise direction in FIG. 3, and the cover 71B of the touch sensor apparatus 61D located on the side surface of the irradiation apparatus 34 comes into contact with the bed 48, the contact thereof is detected by the sensor unit 76 of the touch sensor apparatus 61D, and a contact signal that is output from this sensor unit 76 is output. On the basis of the output contact signal, the gantry control apparatus 113 stops the rotation of the rotary gantry 27. Therefore, the rotation of the irradiation apparatus 34 is stopped, and the irradiation apparatus 34 is not strongly pressed against the bed 48, and a damage in at least one of the irradiation apparatus 34 and the bed 48 can be avoided.

Even in a case where, during rotation of the irradiation apparatus 34, the cover 71B comes into contact with the patient 102 on the bed 48, and the contact thereof is detected by the sensor unit 76 of the touch sensor apparatus 61D, the rotation of the rotary gantry 27 is stopped, and the rotation of the irradiation apparatus 34 is stopped in a similar manner. As a result, this can prevent the patient 102 on the bed 48 from being sandwiched between the rotating irradiation apparatus 34 and the bed 48, and prevents the patient 102 on the bed 48 from being pressed by the irradiation apparatus 34. Therefore, the safety of the patient 102 receiving the treatment with the ion beam can be improved.

Even in a case where the cover 70B of the touch sensor apparatus 61B comes into contact with the bed 48 when the irradiation apparatus 34 rotates in the clockwise direction in FIG. 3, and this contact is detected by the sensor unit 76 of the touch sensor apparatus 61B, a damage in at least one of the irradiation apparatus 34 and the bed 48 can be avoided in the same manner as the case of the touch sensor apparatus 61D. In a case where the cover 70B comes into contact with the patient 102 on the bed 48, the safety of the patient 102 receiving the treatment with the ion beam can be improved in the same manner as the case of the touch sensor apparatus 61D.

In a case where the irradiation apparatus 34 rotates in the counterclockwise direction in FIG. 3, a damage in at least one of the irradiation apparatus 34 and the bed 48 can be avoided because of the function of the touch sensor apparatus 61C having the cover 71A or the touch sensor apparatus 61A having the cover 70A which is the same as the function of the touch sensor apparatus 61D, and further, the safety of the patient 102 receiving the treatment with the ion beam can be improved.

In a case where the contact detection apparatus 82 of the touch sensor apparatus 85 (for example, the contact detection unit 82A located at the support member 84B) comes into contact with the bed 48 during rotation of the irradiation apparatus 34 in the clockwise direction in FIG. 3, the touch sensor 94A arranged at the support member 84B is activated, and the contact signal is output. In this case, the rotation of the irradiation apparatus 34 is stopped in the same manner as the case where the contact signal is output from the sensor unit 76 of the touch sensor apparatus 61D. Therefore, a damage in at least one of the irradiation apparatus 34 and the bed 48 can be avoided. In a case where the contact detection apparatus 82 of the touch sensor apparatus 85 (for example, the contact detection unit 82A located at the support member 84A) comes into contact with the bed 48 during rotation of the irradiation apparatus 34 in the counterclockwise direction in FIG. 3, the touch sensor 94A arranged at the support member 84A is activated, and the contact signal is output. Therefore, the same effects as the case where the contact detection unit 82A located at the support member 84B comes into contact with the bed 48 can be obtained.

In a case where the contact detection unit 82A located at the support member 84B comes into contact with the patient 102 on the bed 48, and in a case where the contact detection unit 82A located at the support member 84A comes into contact with the patient 102 on the bed 48, the rotation of the irradiation apparatus 34 is likewise stopped, so that the safety of the patient 102 receiving the treatment with the ion beam can be improved.

When the patient 102 comes into contact with the contact detection apparatus 82 of the touch sensor apparatus 85 during the movement of the bed 48 on which the patient 102 is lying, the contact signal is output from the touch sensor 94A of the touch sensor apparatus 85. When the contact signal is output, the movement of the bed 48 is stopped. Therefore, the safety of the patient 102 receiving the treatment with the ion beam can be improved.

According to the present embodiment, each of the cover 70A of the touch sensor apparatus 61A, the cover 70B of the touch sensor apparatus 61B, the cover 71A of the touch sensor apparatus 61C, and the cover 71B of the touch sensor apparatus 61D is substantially a contact detection unit detecting a contact with the bed 48 or the patient 102, and is also a side wall of the irradiation apparatus 34 facing the rotation direction of the irradiation apparatus 34 (rotation in the clockwise direction and the rotation in the counterclockwise direction). Therefore, as compared with a case where the touch sensor is attached to the back surface of the cover fixed to the irradiation apparatus 34, the structure of the irradiation apparatus 34 can be simplified.

The covers 70A, 70B, 71A, and 71B are side walls and have large surface area, and therefore, each of the touch sensor apparatuses 61A, 61B, 61C, and 61D can reliably detect, over a side range, a contact between the irradiation apparatus 34 and the bed 48 on which the patient 102 is lying or a contact between the irradiation apparatus 34 and the bed 48.

In the support apparatus supporting the cover (for example, the cover support apparatus 70A supporting the cover 70A and attached to the middle housing unit 53B), a balance weight 73 is attached to the other end portion of the link 74 attached rotatably with the pin 80 to the housing unit of the irradiation apparatus 34 (for example, the middle housing unit 53B) which is at a side opposite to one end portion connected to the connection unit 75 attached to the cover with respect to this pin 80. Therefore, the weight of the cover applied to the one end portion of the link 74 that is connected to the cover can be cancelled by the balance weight 73, and a contact with the bed 48 or the patient 102 can be accurately detected with the touch sensor apparatus attached to the housing unit of the irradiation apparatus 34 (for example, the touch sensor apparatus 61A).

In the embodiment explained above, in order to obtain current tomographic image information, the rotary gantry 27 is rotated while the X ray is discharged from the X ray tube, and the irradiation apparatus 34 attached with the X ray tube is rotated, and the X ray tube discharging the X ray is also rotated around the patient 102 on the bed 48 as described above. In contrast, Japanese Patent Laid-Open No. H1-209077 describes the position determination of the affected area that is performed without rotating the X ray tube discharging the X ray around the patient 102 on the bed 48. The particle beam irradiation system 1 according to the present embodiment can be applied even to the case where the position determination of the affected area is performed as described therein. The rotary gantry 27 is not rotated, and the rotation angle thereof is maintained at 0 degrees.

As described above, each drive apparatus of the treatment bed 39 is controlled by the bed control apparatus 115, and the bed 48 on which the patient 102 lies is moved to a predetermined position. In a case where the bed 48 or the patient 102 comes into contact with the contact detection apparatus 82 of the touch sensor 85 during movement of this bed 48, the contact signal is output as described above. At this occasion, the movement of the bed 48 is stopped. It is assumed that, after the cause of the contact between the bed 48 or the patient 102 and the contact detection apparatus 82 is eliminated, the movement of the bed 48 is controlled by the bed control apparatus 115, and the bed 48 is moved to a position where the bed 48 or the patient 102 does not come into contact with the contact detection apparatus 82. In the state in which the rotation angle of the rotary gantry 27 is zero degrees, the X ray discharged from the X ray tube provided in the irradiation apparatus 34 is irradiated to the affected area of the patient 102 at the position of the bed 48. The X ray having been transmitted through the affected area is detected by the X ray detection apparatus (not shown) located below the bed 48 so as to face the X ray tube provided in the irradiation apparatus 34. The amount of movement of the bed 48 and the rotation angle of the bed 48 in the X-Y plane and the amount of movement of the bed 48 in the X-Z plane are derived by using the X ray detection signal that is output from the X ray detection apparatus as a result of detection of the X ray, as described in Japanese Patent Laid-Open No. H1-209077.

The amount of movement of the bed 48 and the rotation angle of the bed 48 are input into the bed control apparatus 115, and the position of the bed 48 is determined. Thereafter, as described above, the rotary gantry 27 is rotated so that the center axis 107 of the irradiation apparatus 34 matches the irradiation direction of the ion beam to the affected area. In a case where any one of the covers 70A, 70B, 71A, and 71B and the contact detection apparatus 82 of the irradiation apparatus 34 comes into contact with the bed 48 or the patient 102 while the rotary gantry 27 is rotated in order to cause the center axis 107 of the irradiation apparatus 34 to match the irradiation direction of the ion beam to the affected area, the contact thereof is detected as described above, and the rotation of the rotary gantry 27 or the movement of the bed 48 is stopped. The cause of this contact is eliminated, and the rotary gantry 27 is rotated so that the center axis 107 of the irradiation apparatus 34 matches the irradiation direction of the ion beam to the affected area, and thereafter, as described above, the ion beam that is output from the synchrotron accelerator 3 is irradiated from the irradiation apparatus 34 to the affected area of the patient 102 on the bed 48.

Even in a case where the position of the affected area is determined as described in Japanese Patent Laid-Open No. H1-209077, each of the effects as explained above can be obtained by applying the particle beam irradiation system 1 according to the present embodiment.

Second Embodiment

A particle beam irradiation system according to the second embodiment which is another preferred embodiment of the present invention will be hereinafter explained with reference to FIG. 16.

The particle beam irradiation system 1 according to the first embodiment uses the ion beam generation apparatus 2 including the synchrotron accelerator 3 as the ion beam generation apparatus, but a particle beam irradiation system 1A according to the present embodiment uses an ion beam generation apparatus 2A including a cyclotron accelerator 119 as an ion beam generation apparatus.

Figure 16:
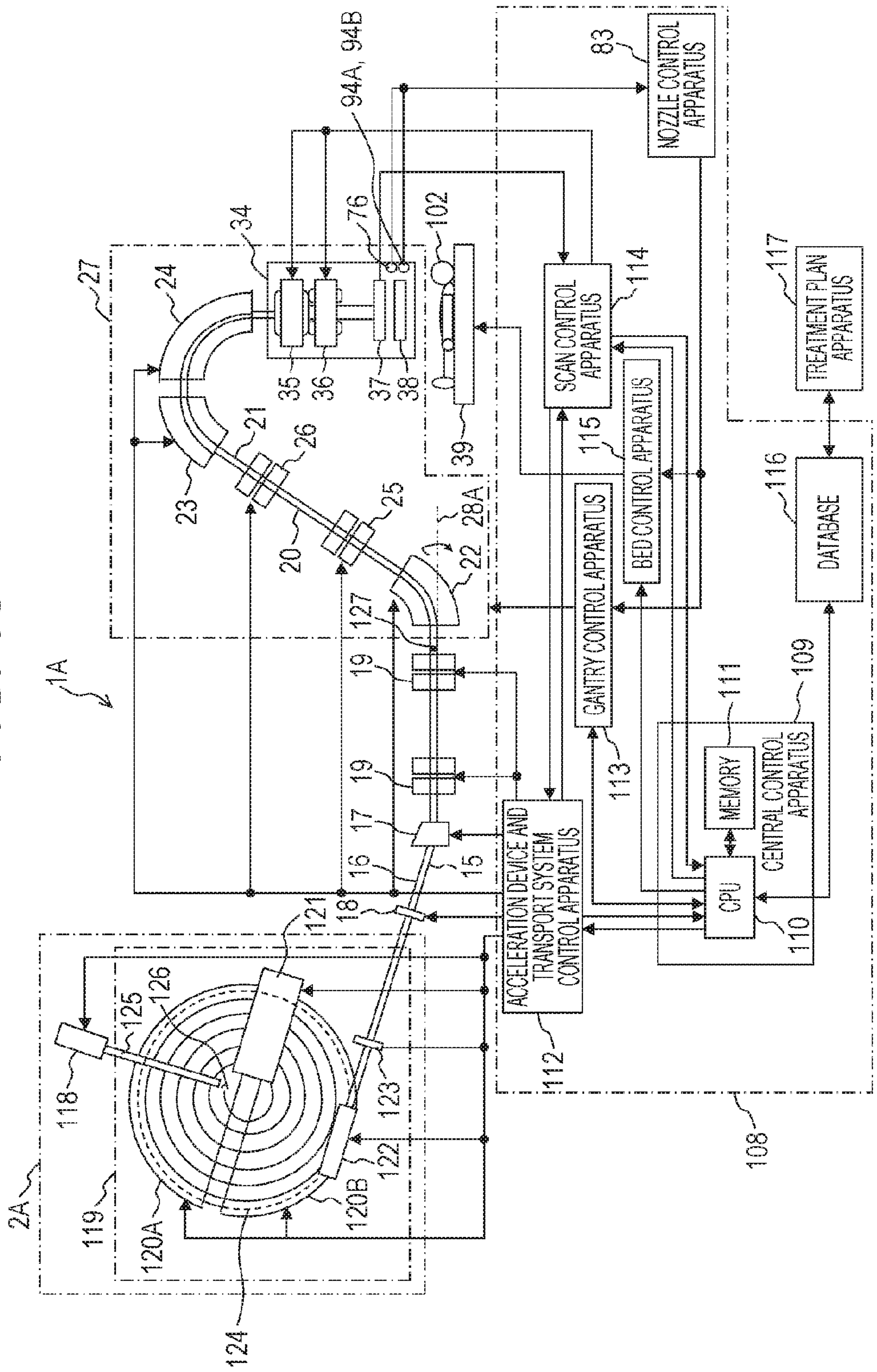
FIG. 16 is a configuration diagram illustrating a particle beam irradiation system according to a second embodiment which is another preferred embodiment of the present invention.

As illustrated in FIG. 16, the particle beam irradiation system 1A includes an ion beam generation apparatus 2A, an HEBT system 15, a GABT system 20, a rotary gantry 27, an irradiation apparatus 34, and a control system 108. The configurations of the HEBT system 15, the GABT system 20, the rotary gantry 27, and the irradiation apparatus 34 are the same as the configurations of those in the particle beam irradiation system 1 according to the first embodiment.

Hereinafter, the ion beam generation apparatus 2A that is different from the particle beam irradiation system 1 will be mainly explained.

The ion beam generation apparatus 2A includes an ion source 118 and a cyclotron accelerator 119. The cyclotron accelerator 119 includes a round vacuum container 124, polarization electromagnets 120A and 120B, a radiofrequency acceleration apparatus 121, and a septum electromagnet 122 for extraction. A vacuum duct 125 connected to the ion source 118 extends to a center position of the vacuum container 124, and is connected to the vacuum container 124. The electrode 126 for incidence that is bent on the horizontal plane is disposed in proximity to the open end of the vacuum duct 125 in the vacuum container 124. Each of the polarization electromagnets 120A and 120B is in a semicircular shape, and the polarization electromagnets 120A and 120B are disposed so that the straight line portions thereof face each other, so that the upper surface and the lower surface of the vacuum container 124 are covered.

The septum electromagnet 122 provided at an ion beam output port of the vacuum container 124 is connected to the beam path 16 of the HEBT system 15. A degrader 123 having multiple metal plates is attached to a beam path 16 between the septum electromagnet 122 and the quadrupole electromagnet 18. The degrader 123 has a function for adjusting the energy of the ion beam emitted from the cyclotron accelerator 119, and has multiple metal plates (not shown) having different thicknesses. These metal plates can move in a direction perpendicular to the beam path 16. By inserting one or multiple metal plates having different thicknesses into the beam path 16 so as to cross the beam path 16, the amount of attenuation of the energy of the ion beam passing through the beam path 16 is controlled. As a result, the energy of the ion beam irradiated on the affected area of the patient 102 can be changed, and the ion beam can be irradiated to each layer existing in a depth direction of the affected area.

In the present embodiment, the touch sensor apparatuses 61A, 61B, 61C, and 61D, and the touch sensor apparatus 85 provided in the irradiation apparatus 34 also function in the same manner as those in the particle beam irradiation system 1 according to the first embodiment.

The particle beam irradiation system 1A according to the present embodiment can obtain each of the effects obtained from the first embodiment.

What is claimed is:

1. A particle beam irradiation system comprising:
- an accelerator accelerating an ion beam; and
- an irradiation apparatus guiding the ion beam emitted from the accelerator,
- wherein the irradiation apparatus includes one or more first touch sensor apparatuses, each respectively detecting a force applied from a direction crossing a center axis of the irradiation apparatus,
- wherein each of the one or more first touch sensor apparatuses respectively includes:
- a cover;
- a plurality of cover support apparatuses, each respectively including a fixing member attached to the irradiation apparatus, a link rotatably attached to the cover and rotatably attached to the fixing member, and a counterweight attached to the link, and
- a plurality of switches each disposed between the fixing member and the link of one of the cover support apparatuses to detect the force applied to the cover from the direction crossing the center axis of the irradiation apparatus.

2. The particle beam irradiation system according to claim 1, further comprising:
- a rotary gantry which rotates the irradiation apparatus around a center line thereof,
- wherein the cover of each the one or more first touch sensor apparatuses faces a rotary direction of the irradiation apparatus.

3. The particle beam irradiation system according to claim 1, wherein the first touch sensor apparatuses are disposed on at least one of a middle housing and a lower housing of the irradiation apparatus.

4. The particle beam irradiation system according to claim 3, further comprising:
- a second touch sensor apparatus disposed on a lower housing of the irradiation apparatus,
- wherein the second touch sensor apparatus includes a contact bar disposed around the center axis at a tip of the lower housing, a first support member to which the contact bar is connected, a plurality of sensors attached to the first support member, and a plurality of springs which attach the first support member to the lower housing and pull the first support member into contact with the sensors.

5. The particle beam irradiation system according to claim 1, further comprising:
- a rotary gantry which rotates the irradiation apparatus around a center line thereof; and
- a second touch sensor apparatus disposed on a lower housing of the irradiation apparatus,
- wherein the cover of each the one or more first touch sensor apparatuses faces a rotary direction of the irradiation apparatus, and
- wherein the second touch sensor apparatus includes a contact bar disposed around the center axis at a tip of the lower housing, a first support member to which the contact bar is connected, a plurality of sensors, and a plurality of springs which attach the first support member to the lower housing and pull the first support member into contact with the sensors.

6. The particle beam irradiation system according to claim 5, wherein the cover is a side wall of the irradiation apparatus and moves in accordance with a contact with an object or a patient.

7. The particle beam irradiation system according to claim 6, wherein a pair of the first touch sensor apparatuses face rotation directions of the irradiation apparatus.

8. The particle beam irradiation system according to claim 5, wherein the counterweight is disposed on a first end of the link opposite a second end to which the cover is attached.

9. The particle beam irradiation system according to claim 5, wherein the force applied to the cover activates the switch in accordance with a movement of the cover in the direction towards the center axis.

10. The particle beam irradiation system according to claim 9, wherein the counterweight is attached to the link on a side facing the center axis of the irradiation apparatus, and cover support apparatus includes a balance weight, wherein the link member is rotatably attached to the cover and to fixing member by a pair of pins.

11. The particle beam irradiation system according to claim 10, wherein the switches are each disposed on the fixing member of the cover support apparatuses.

12. The particle beam irradiation system according to claim 5, wherein the irradiation apparatus includes a collimator accommodation unit disposed at a tip of the irradiation apparatus and attached to the lower housing, and wherein the second touch sensor apparatus is disposed away from an apical surface of the collimator accommodation unit in the center axis direction of the irradiation apparatus.

13. The particle beam irradiation system according to claim 12, wherein the second touch sensor apparatus is held on the collimator accommodation unit by a plurality of L-shaped second support members.

14. The particle beam irradiation system according to claim 12, wherein the springs are attached to the L-shaped second support members.

15. The particle beam irradiation system according to claim 14, wherein the sensors each include a first sensor unit attached to the first support member, and a second sensor unit attached to one of the L-shaped second support members.

16. The particle beam irradiation system according to claim 14, wherein the second touch sensor apparatus includes a plurality of slide mechanisms each including a guide member and a position member, wherein the guide member is attached to the first support member, and the position member is attached to one of the L-shaped second support members, and wherein the position determination member is inserted into a hole portion formed in the guide member and having a guide surface formed on an inner surface thereof.

17. The particle beam irradiation system according to claim 14, wherein the second touch sensor apparatus includes a plurality of slide mechanisms each including a guide member and a position member, wherein the guide member is attached to one of the L-shaped second support members, and the position member is attached to the first support member, and wherein the position determination member is inserted into a hole portion formed in the guide member and having a guide surface formed on an inner surface thereof.

* * * * *